United States Patent
Luukko et al.

(10) Patent No.: US 11,602,566 B2
(45) Date of Patent: Mar. 14, 2023

(54) MEDICAL PRODUCT COMPRISING A BIOACTIVE MOLECULE IMMOBILIZED TO NANOFIBRILLAR CELLULOSE, AND A METHOD FOR PREPARING THEREOF

(71) Applicant: UPM-Kymmene Corporation, Helsinki (FI)

(72) Inventors: Kari Luukko, Espoo (FI); Markus Nuopponen, Helsinki (FI); Nicolò Curzio, Tribano (IT); Marjo Yliperttula, Espoo (FI); Polina Ilina, Vantaa (FI); Päivi Tammela, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 73 days.

(21) Appl. No.: 16/771,518

(22) PCT Filed: Mar. 1, 2019

(86) PCT No.: PCT/EP2019/055097
§ 371 (c)(1),
(2) Date: Jun. 10, 2020

(87) PCT Pub. No.: WO2019/166606
PCT Pub. Date: Sep. 6, 2019

(65) Prior Publication Data
US 2021/0170041 A1 Jun. 10, 2021

(30) Foreign Application Priority Data
Mar. 2, 2018 (EP) .................................... 18397510

(51) Int. Cl.
| A61K 47/61 | (2017.01) |
| A61K 38/46 | (2006.01) |
| A61L 15/28 | (2006.01) |
| A61L 15/44 | (2006.01) |
| C12N 11/12 | (2006.01) |

(52) U.S. Cl.
CPC .............. *A61K 47/61* (2017.08); *A61K 38/46* (2013.01); *A61L 15/28* (2013.01); *A61L 15/44* (2013.01); *C12N 11/12* (2013.01); *A61L 2300/404* (2013.01)

(58) Field of Classification Search
CPC ......... A61K 47/61; A61L 15/28; A61L 15/44; A61L 2300/404; A61L 2400/12
See application file for complete search history.

(56) References Cited

U.S. PATENT DOCUMENTS

| 4,576,817 A | 3/1986 | Montgomery et al. |
| 2003/0021821 A1* | 1/2003 | Fertala ................ A61K 9/0024 514/17.2 |
| 2004/0241436 A1 | 12/2004 | Hsieh et al. |
| 2009/0221047 A1* | 9/2009 | Schindler ............... B01D 39/14 435/253.6 |
| 2015/0203594 A1* | 7/2015 | Orelma ................ C07K 14/765 536/63 |
| 2016/0289894 A1* | 10/2016 | Kajanto ................. D21C 9/002 |

FOREIGN PATENT DOCUMENTS

| WO | 2012056111 A2 | 5/2012 |
| WO | WO-2014128354 A1 * | 8/2014 ............ A61L 15/28 |
| WO | 2016057788 A1 | 4/2016 |
| WO | 2016128620 A1 | 8/2016 |
| WO | 2017174874 A1 | 10/2017 |

OTHER PUBLICATIONS

Karabulut, E. et al. "Adhesive Layer-by-Layer Films of Carboxymethylated Cellulose Nanofibril-Dopamine Covalent Bioconjugates Inspired by Marine Mussel Threads" ACSNano 2012, 6(6), 4731-4739 (Year: 2012).*
Karabulut, E. et al. "Adhesive Layer-by-Layer Films of Carboxymethylated Cellulose Nanofibril-Dopamine Covalent Bioconjugates Inspired by Marine" ACS Nano 2012, 6 (6), 4731-4739 (Year: 2012).*
Arola, S. et al., "Immobilization—Stabilization of Proteins on Nanofibrillated Cellulose Derivatives and Their Bioactive Film Formation", Biomacromolecules, vol. 13, 2012; pp. 594-603.
Karabulut, E. et al., "Adhesive Layer-by-Layer Films of Carboxymethylated Cellulose Nanofibril-Dopamine Covalent Biioconjugates Inspired by Marine Mussel Threads", American Chemical Society, vol. 6, No. 6, 2012; pp. 4731-4739.
Leppiniemi, J. et al., "3D-Prinatable Bioactivated Nanocellulose-Alginate Hydrogels", ACS Applied Materials and Interfaces, vol. 9; published: Jun. 9, 2017; pp. 21959-21970.
Sulaiman, S. et al., "A Review: Potential Usage of Cellulose Nanofibers (CNF) for Enzyme Immobilization via Covalent Interactions", Appl. Biochem Biotechnol. vol. 175, 2015; pp. 1817-1842.
International Search Report for the corresponding International Application No. PCT/EP2019/055097; International Filing Date: Mar. 1, 2019; dated May 10, 2019; 5 pages.
Written Opinion for the corresponding International Application No. PCT/EP2019/055097; International Filing Date: Mar. 1, 2019; dated May 10, 2019; 8 pages.

* cited by examiner

*Primary Examiner* — Andrew S Rosenthal
(74) *Attorney, Agent, or Firm* — Cantor Colburn LLP

(57) ABSTRACT

The present application provides a method for preparing a medical product for covering tissue, the method comprising providing nanofibrillar cellulose, providing a bioactive molecule, and covalently bonding the bioactive molecule to the nanofibrillar cellulose. The present application also provides a medical product for covering tissue comprising a bioactive molecule covalently bound to nanofibrillar cellulose.

26 Claims, 10 Drawing Sheets

1

2

3

4

MEDICAL PRODUCT COMPRISING A BIOACTIVE MOLECULE IMMOBILIZED TO NANOFIBRILLAR CELLULOSE, AND A METHOD FOR PREPARING THEREOF

CROSS-REFERENCE TO RELATED APPLICATIONS

This application is a National Stage application of PCT/EP2019/055097, filed Mar. 1, 2019, which claims priority to European Application No. 18397510.1 filed on Mar. 2, 2018, both of which are incorporated by reference herein in their entirety.

TECHNICAL FIELD

The present application relates to medical products comprising nanofibrillar cellulose, and to methods for preparing thereof. More particularly the present application relates to medical products containing an immobilized bioactive molecule.

BACKGROUND

Chronic wounds are a growing medical problem that cause high rates of concern and mortality, costing the healthcare industry worldwide millions of dollars. Chronic wound healing is hampered by the presence of bacterial infections that form biofilms, in which the bacteria are able to grow and exert their pathogenicity, leading to the development of a chronic infection. Bacterial biofilms make chronic wounds more refractory to treatment and slow tissue repair by stimulating chronic inflammation at the wound site. Biofilm-associated cutaneous diseases are a growing concern and therefore in the United States each year 1.96 million people are affected by biofilm-related infections. In addition, the mortality rate is 268000 patients annually.

Above all, the risk is described by three main negative outcomes of biofilm deposition within the wound bed: bacteria are protected from host defences, damaged tissue regeneration is suppressed and antibiotic treatment efficacy is repressed. It appears inequivocal that if the biofilm deposition is prevented, the wound healing process is hastened and advanced.

The usage of antibiotics as the exclusory answer to biofilm-related cutaneous diseases has several drawbacks, including development of antibiotic resistance, inefficient antibiotic concentration at wound bed and interaction with systemic circulation.

There is a need for efficient medical products for treating wounds or other conditions of skin or other tissue. The products should be biocompatible with the tissue and provide conditions facilitating healing of the area in the need of treatment, such as a wound. Use of antibiotics should be avoided. It may not be desired to release any active substances to the circulation of the subject to be treated.

SUMMARY

An approach disclosed herein solves many limitations related to common approaches. In one example quorum quenching enzymes were immobilized to medical devices wherein they promote prolonged biofilm inhibition, with the resultant resolution of chronic biofilm infections. This principle can be applied to other immobilizable substances and uses as well. The nanofibrillar cellulose hydrogel acts as an efficient matrix for immobilized bioactive substances, and such immobilized bioactive substances may be provided to a variety of targets.

With the immobilized substances products useful in medical, scientific, cosmetic or other fields as described herein can be obtained. The substances may be bioactive molecules, for example proteins, such as enzymes, other proteins, peptides, hormones, cytokines, photosensitizing molecules, anti-cancer drugs and the like molecules or substances exhibiting biological activity or being able to interact with a counterpart exhibiting or linked to biological activity.

The present application provides a method for preparing a medical product, the method comprising
    providing nanofibrillar cellulose,
    providing a bioactive molecule, and
    covalently bonding the bioactive molecule to the nanofibrillar cellulose.

The present application also provides a medical product comprising a bioactive molecule covalently bound to nanofibrillar cellulose. The medical product may be obtained with the methods disclosed herein.

The main embodiments are characterized in the independent claims. Various embodiments are disclosed in the dependent claims. The embodiments recited in claims and in the specification are mutually freely combinable unless otherwise explicitly stated.

It was found out that bioactive molecules, especially enzymes, which are immobilized in nanofibrillar cellulose, remain stable and bioactive over a long period of time. The bioactive molecules are not released from the matrix so they do not enter the circulation of the subject to be treated, and the bioactivity remains available for long periods. This was achieved especially when the bioactive molecules were covalently bound to the nanofibrillar cellulose. Specifically when enzymes are covalently immobilized to nanofibrillar cellulose, their stability and activity may be even improved. The other advantageous properties of nanofibrillar cellulose support and enhance the effects of the bioactive molecules to the target.

Nanofibrillar cellulose is ideal matrix for covalent binding of bioactive molecules, which may be carried out via carboxylic groups. Nanofibrillar cellulose may contain or may be modified to contain a high number of carboxylic groups, which together with the large surface area of the fibrillated material enables covalent bonding of high number of bioactive molecules therefore providing high bioactivity in the final product.

The medical products described herein are useful in medical applications, wherein the materials comprising nanofibrillar cellulose are in contact with living tissue. It was discovered that nanofibrillar cellulose provides advantageous properties when it is applied for example onto skin or onto a damaged area. The products containing nanofibrillar cellulose as described herein are highly biocompatible with the living tissue and provide several advantageous effects. Without bonding to any specific theory, it is believed that the medical product comprising nanofibrillar cellulose provides a very hydrophilic surface, which, when applied against a skin or other tissue, for example a wound, absorbs and retains water from the tissue and forms a water film between the medical product and the tissue thus creating conditions promoting the healing of the wound. The medical product may be also moistened to enhance the effect. This effect together with the high content of immobilized bioactive molecules makes the medical products described herein extremely efficient for treating tissue.

When the medical products are used for covering tissue, such as skin, especially containing wounds or other damages or injuries, for example in products such as gels, plasters, dressings, medical patches or parts of plasters, patches or dressings, several effects are provided. The usability of the products is good as the product may be applied and removed easily without being damaged, for example torn. The product may also be cut into a desired size and shape without affecting the properties thereof. When used for covering wounds the material of the product acts as an artificial skin, which protects the wound and will come loose when the wound heals. The medical product will not attach to a damaged area in such irreversible way as conventional materials, which are usually very difficult to remove without damaging the healed area. The conditions between the medical product and the tissue facilitate the healing of a damaged area.

The medical products of the embodiments are advantageous in the treatment of grafts, such as skin graft. The medical product may be used for covering the graft area and it acts as a protective layer. As the graft heals, the product forms a scab-like structure, which promotes the healing.

The immobilized bioactive molecules may not be only applied to wounds or grafts, but any other area of skin or other tissue requiring treatment or being able to receive treatment may be treated as well. Such areas may include damaged tissues, tissues containing tumours, skin disorder or disease areas, and the like. The immobilized bioactivity may be also directed to healthy skin or other tissue.

The products involving quorum quenching molecules may be used to suppress or prevent bacterial biofilm formation. This may be used to overcome for example antibody, leukocyte and/or antibiotic resistance, which are connected to the biofilm formation.

DETAILED DESCRIPTION

Figure 1:
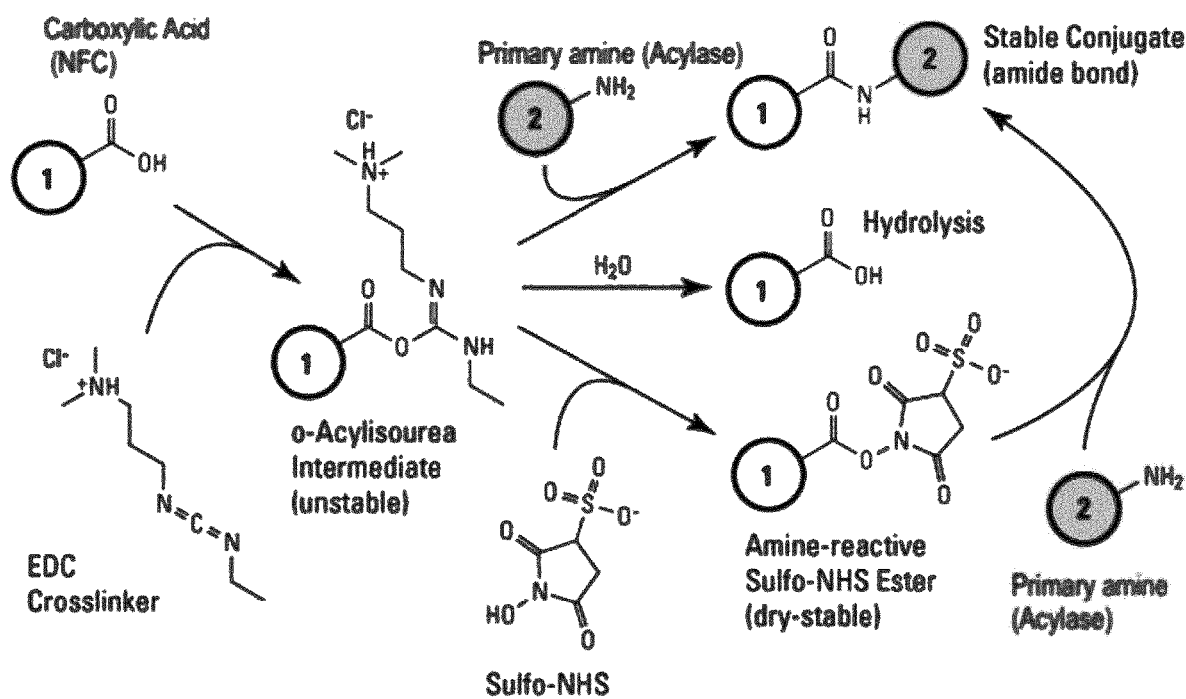
FIG. 1 shows an immobilization scheme of acylase with EDC and sulfo-NHS
Figure 2:
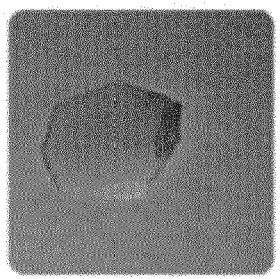
FIG. 2 shows different nanocellulose and cellulose membranes tested. 1=LOT 11885, 2=LOT 11888, 3=Growdex T LOT 119671917. 4=Medical grade cellulose gauze (Pur-Zellin Hartmann)
Figure 2:
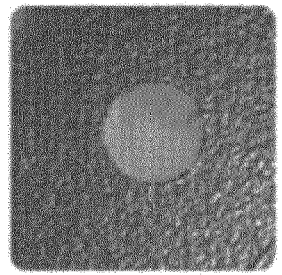
Figure 2:
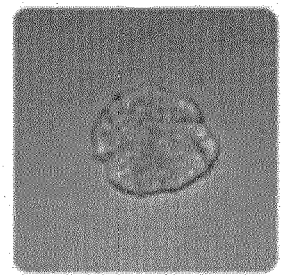
Figure 2:
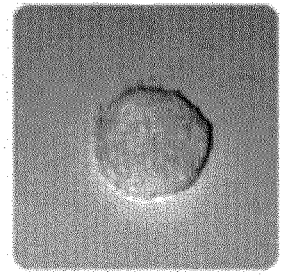

In this specification, percentage values, unless specifically indicated otherwise, are based on weight (w/w). If any numerical ranges are provided, the ranges include also the upper and lower values. The concentrations are presented as dry weight, unless indicated otherwise.

The present application discloses medical products comprising one or more bioactive molecule(s) immobilized to nanofibrillar cellulose, which acts as a nanocellulose nanofiber matrix or scaffold. Nanofibrillar cellulose is a nanoscale material based on cellulose that shows unique physical characteristics such as high surface area, mechanical strength and peculiar morphology. Additionally, the material was proven to be biocompatible.

One example described herein relates to a medical product or device comprising an anti-bacterial nanofiber matrix modified with a covalently immobilized quorum quenching enzyme. On one side, the device aims to promote wound healing due to nanocellulose distinctive properties such as biocompatibility and surface properties; on the other side, quorum quenching activity cleaves bacterial signalling molecules, and prevents or suppresses biofilm deposition in the wound. It is an efficient and a cost-effective approach to facilitate complete healing of chronic wounds, due to a reduced biofilm deposition and weakened bacterial virulence within the wound bed.

Medical Products

The present application provides medical products, which may be applied onto the skin or other tissue of a target or a subject, such as a patient or a person, human or animal, suffering from a condition. The medical products may be provided as gels, patches, plasters, bandages or the like, which may be applied onto a wound or onto damaged area or onto an area or a target requiring treatment. The present application also provides methods for preparing the medical products.

The term "medical" refers to a product or use wherein the product, i.e. a product comprising the nanofibrillar cellulose (NFC) of the embodiments, is used or is suitable for medical purposes or for scientific purposes, for example for treatment or for research. A medical product may be sterilized, or it is sterilizable, before and/or after immobilizing the bioactive molecule, for example by using temperature, pressure, moisture, chemicals, radiation or a combination thereof. The product, preferably the hydrogel with the attached molecule(s), may be for example autoclaved, or other methods using high temperature may be used, in which cases the product should tolerate high temperatures over 100° C., for example at least 121° C. or 134° C. In one example the product is autoclaved at 121° C. for 15 minutes. It is also desired that a medical product is pyrogen free and it does not contain undesired protein residues or the like. A medical product is preferably non-toxic to the target. Also UV sterilization may be used.

Nanofibrillar Cellulose

The starting material for the preparation process is usually nanofibrillar cellulose obtained from the disintegration of fibrous raw material and existing at a relatively low concentration homogeneously distributed in water due to the disintegration conditions. The starting material may be an aqueous gel at a concentration of 0.2-10% (w/w), for example 0.2-5% (w/w). The nanofibrillar cellulose may be obtained directly from the disintegration of fibrous raw material.

The nanofibrillar cellulose is prepared generally from cellulose raw material of plant origin. The raw material may be based on any plant material that contains cellulose. The raw material may also be derived from certain bacterial fermentation processes. The nanofibrillar cellulose is preferably made of plant material. In one example the fibrils are obtained from non-parenchymal plant material. In such case the fibrils may be obtained from secondary cell walls. One abundant source of such cellulose fibrils is wood fibres. The nanofibrillar cellulose is manufactured by homogenizing wood-derived fibrous raw material, which may be chemical pulp. Cellulose fibers are disintegrated to produce fibrils which have an average diameter of only some nanometers, which may be 200 nm at the most, and gives a dispersion of fibrils in water. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging. In general in the cellulose sources from primary cell walls, such as sugar beet, potato tuber and banana rachis, the microfibrils are easier to liberate from the fibre matrix than fibrils from wood, and the disintegration requires less energy. However, these materials are still somewhat heterogeneous and consist of large fibril bundles.

It was found out that nanofibrillar cellulose obtained from wood cellulose is preferable for medical products described herein. Wood cellulose is available in large amounts, and the preparation methods developed for wood cellulose enable producing nanofibrillar materials suitable for medical products. Nanofibrillar cellulose obtained from wood also exhibit properties which are preferred in medical products. Wood may be from softwood tree such as spruce, pine, fir, larch, douglas-fir or hemlock, or from hardwood tree such as birch, aspen, poplar, alder, *eucalyptus*, oak, beech or acacia, or from a mixture of softwoods and hardwoods. In one embodiment the nanofibrillar cellulose is obtained from wood pulp. In one embodiment the nanofibrillar cellulose is obtained from hardwood pulp. In one example the hardwood is birch. In one embodiment the nanofibrillar cellulose is obtained from softwood pulp. In one embodiment said wood pulp is chemical pulp. Chemical pulp may be desired for medical products. Chemical pulp is pure material and may be used in a wide variety of applications. For example chemical pulp lack the pitch and resin acids present in mechanical pulp, and it is more sterile or easily sterilisable. Further, chemical pulp is more flexible and provides advantageous properties for example in medical patches or dressings and other materials applied on living tissue.

As used herein, the term "nanofibrillar cellulose" refers to cellulose fibrils or fibril bundles separated from cellulose-based fiber raw material. These fibrils are characterized by a high aspect ratio (length/diameter). The average length of nanofibrillar cellulose (the median length of particles such as fibrils or fibril bundles) may exceed 1 µm, and in most cases it is 50 µm or less. If the elementary fibrils are not completely separated from each other, the entangled fibrils may have an average total length for example in the range of 1-100 µm, 1-50 µm, or 1-20 µm. However, if the nanofibrillar material is highly fibrillated, the elementary fibrils may be completely or almost completely separated and the average fibril length is shorter, such as in the range of 1-10 µm or 1-5 µm. This applies especially for native grades of fibrils which are not shortened or digested, for example chemically, enzymatically or mechanically. However, strongly derivatized nanofibrillar cellulose may have a shorter average fibril length, such as in the range of 0.3-50 µm, such as 0.3-20 µm, for example 0.5-10 µm or 1-10 µm. Especially shortened fibrils, such as enzymatically or chemically digested fibrils, or mechanically treated material, may have an average fibril length of less than 1 µm, such as 0.1-1 µm, 0.2-0.8 µm or 0.4-0.6 µm. The fibril length and/or diameter may be estimated microscopically, for example using CRYO-TEM, SEM or AFM images.

The average diameter (width) of nanofibrillar cellulose is less than 1 µm, or 500 nm or less, such as in the range of 1-500 nm, typically 200 nm or less, such as in the range of 1-200 nm, 2-200 nm, 2-100 nm, or 2-50 nm, even 2-20 for highly fibrillated material. The smallest fibrils are in the scale of elementary fibrils, the average diameter being typically in the range of 2-12 nm. The dimensions and size distribution of the fibrils depend on the refining method and efficiency. In case of native nanofibrillar cellulose, the average diameter of a fibril may be in the range of 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose obtained from plants, especially wood, may also contain small amounts of other plant components, especially wood components, such as hemicellulose or lignin. The amount is dependent on the plant source. Often used parallel names for nanofibrillar cellulose include nanofibrillated cellulose (NFC) and nanocellulose.

In general cellulose nanomaterials may be divided into categories according to TAPPI W13021, which provides standard terms for cellulose nanomaterials. Two main categories are "Nano objects" and "Nano structured materials". Nanostructured materials include "Cellulose microcrystals" (sometimes called as CMC) having a diameter of 10-12 µm and length:diameter ratio (L/D)<2, and "Cellulose microfibrils" having a diameter of 10-100 nm and a length of 0.5-50 µm. Nano objects include "Cellulose nanofibers", which can be divided into "Cellulose nanocrystals" (CNC) having a diameter of 3-10 nm and L/D>5, and "Cellulose nanofibrils" (CNF or NFC), having a diameter of 5-30 nm and L/D>50.

Different grades of nanofibrillar cellulose may be categorized based on three main properties: (i) size distribution, length and diameter (ii) chemical composition, and (iii) rheological properties. To fully describe a grade, the properties may be used in parallel. Examples of different grades include native (or non-modified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low degree of substitution, low viscosity vs. high viscosity etc. The fibrillation technique and the chemical pre-modification have an influence on the fibril size distribution. Typically, non-ionic grades have wider average fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood vs. softwood pulp, different polysaccharide composition exists in the final nanofibrillar cellulose product. Commonly, the non-ionic grades are prepared from bleached birch pulp, which yields high xylene content (25% by weight). Modified grades are prepared either from hardwood or softwood pulps. In those modified grades, the hemicelluloses are also modified together with the cellulose domain. Most probably, the modification is not homogeneous, i.e. some parts are more modified than others. Thus, detailed chemical analysis is usually not possible as the modified products are complicated mixtures of different polysaccharide structures.

In an aqueous environment, a dispersion of cellulose nanofibers forms a viscoelastic hydrogel network. The gel is formed already at relatively low concentrations of for example 0.05-0.2% (w/w) by dispersed and hydrated entangled fibrils. The viscoelasticity of the NFC hydrogel may be characterized for example with dynamic oscillatory rheological measurements.

The nanofibrillar cellulose hydrogels exhibit characteristic rheological properties. For example they are shear-thinning or pseudoplastic materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent for example on the raw material, the disintegration method and number of disintegration runs. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment is performed at conditions wherein water is sufficiently present to prevent the formation of bonds between the fibers.

In one example the disintegration is carried out by using a disperser having at least one rotor, blade or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives a plurality of successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex device.

Another example of a device suitable for disintegrating is a pin mill, such as a multi-peripheral pin mill. One example of such device, as described in U.S. Pat. No. 6,202,946 B1, includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one embodiment the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The energy taken by the refining work is normally expressed in terms of energy per processed raw material quantity, in units of e.g. kWh/kg, MWh/ton, or units proportional to these. The expressions "disintegration" or "disintegration treatment" may be used interchangeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be for example Brookfield viscosity or zero shear viscosity. The specific viscosity, as described herein, distinguishes nanofibrillar cellulose from non-nanofibrillar cellulose.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used.

The nanofibrillar cellulose provided as a starting material in the method may be characterized by the viscosity it provides in a water solution. The viscosity describes, for example, the fibrillation degree of the nanofibrillar cellulose. In one embodiment the nanofibrillar cellulose when dispersed in water provides a Brookfield viscosity of at least 2000 mPa·s, such as at least 3000 mPa·s, measured at a consistency of 0.8% (w/w) and at 10 rpm. In one embodiment the nanofibrillar cellulose, when dispersed in water, provides a Brookfield viscosity of at least 10000 mPa·s measured at a consistency of 0.8% (w/w) and at 10 rpm. In one embodiment the nanofibrillar cellulose, when dispersed in water, provides a Brookfield viscosity of at least 15000 mPa·s measured at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at a consistency of 0.8% (w/w) and at 10 rpm.

In one embodiment the nanofibrillar cellulose comprises non-modified nanofibrillar cellulose. In one embodiment the nanofibrillar cellulose is non-modified nanofibrillar cellulose. The drainage of non-modified nanofibrillar cellulose is significantly faster than for example anionic grade. Non-modified nanofibrillar cellulose generally has a Brookfield viscosity in the range of 2000-10000 mPa·s, measured at a consistency of 0.8% (w/w) and at 10 rpm.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, i.e. pulp.

The modification treatment to the fibers may be chemical, enzymatic or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface.

The cellulose in the fibers may be especially ionically charged after the modification. The ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. Chemical modifications introducing groups, such as carboxyl groups, which may take part in forming a covalent bond between the nanofibrillar cellulose and the bioactive molecule, may be desired. A cationic charge in turn may be created chemically by cationization by attaching a cationic group to the cellulose, such as quaternary ammonium group.

In one embodiment the nanofibrillar cellulose comprises chemically modified nanofibrillar cellulose, such as anionically modified nanofibrillar cellulose or cationically modified nanofibrillar cellulose. In one embodiment the nanofibrillar cellulose is anionically modified nanofibrillar cellulose. In one embodiment the nanofibrillar cellulose is cationically modified nanofibrillar cellulose. In one embodiment the anionically modified nanofibrillar cellulose is oxidized nanofibrillar cellulose. In one embodiment the anionically modified nanofibrillar cellulose is sulphonized nanofibrillar cellulose. In one embodiment the anionically modified nanofibrillar cellulose is carboxymethylated nanofibrillar cellulose. It was found out that anionic grade provided the most suitable properties for medical products described herein. Also native grade was useful.

The cellulose may be oxidized. In the oxidation of cellulose, the primary hydroxyl groups of cellulose may be oxidized catalytically by a heterocyclic nitroxyl compound, such as through N-oxyl mediated catalytic oxidation, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

In one embodiment such chemically modified nanofibrillar cellulose, when dispersed in water, provides a Brookfield viscosity of at least 10000 mPa·s measured at a consistency of 0.8% (w/w) and at 10 rpm. In one embodiment such chemically modified nanofibrillar cellulose, when dispersed in water, provides a Brookfield viscosity of at least 15000 mPa·s measured at a consistency of 0.8% (w/w) and at 10 rpm. In one embodiment such chemically modified nanofibrillar cellulose, when dispersed in water, provides a Brookfield viscosity of at least 18000 mPa·s measured at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one embodiment the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at a consistency of 0.8% (w/w) and at 10 rpm.

In one embodiment the nanofibrillar cellulose comprises chemically unmodified nanofibrillar cellulose. In one embodiment such chemically unmodified nanofibrillar cellulose, when dispersed in water, provides a Brookfield viscosity of at least 2000 mPa·s, or at least 3000 mPa·s, measured at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one example nanofibrillar cellulose suitable for use in the medial products described herein has an average diameter of a fibril in the range of 1-200 nm, or 1-100 nm. In one example said nanofibrillar cellulose has an average diameter of a fibril in the range of 1-50 nm, such as 5-30 nm. In one example said nanofibrillar cellulose has an average diameter of a fibril in the range of 2-15 nm, such as in the case of TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

In one example a rheometer viscosity of the nanofibrillar cellulose dispersion is measured at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of $1000\ s^{-1}$ is exceeded. This method may be used for determining the zero-shear viscosity.

In one example the nanofibrillar cellulose, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at a consistency of 0.1% (w/w) in aqueous medium, and measured by nephelometry. To characterize the nanofibrillar cellulose these ranges may be combined with the viscosity ranges of the nanofibrillar cellulose, such as nanofibrillar cellulose which, when dispersed in water, provides a Brookfield viscosity of at least 2000 mPa·s, at least 3000 mPa·s, at least 5000 mPa·s, such as at least 10000 mPa·s, for example at least 15000 mPa·s measured at a consistency of 0.8% (w/w) and at 10 rpm.

Any of the nanofibrillar cellulose described in previous may be used for preparing the medical products discussed herein. The nanofibrillar cellulose may be dewatered to a desired moisture or dry content.

The initial concentration of the nanofibrillar cellulose dispersion, usually aqueous dispersion, which is used as a starting material for preparing the medical products, may be in the range of 0.1-10%. However, it is usually not higher than 5%, such as in the range of 0.3-5.0%, for example in the range of 0.8-1.2%. This is usually the initial concentration of the nanofibrillar cellulose at the exit of the manufacturing process where it is manufactured by disintegrating fibrous raw material. However, it is possible that the nanofibrillar cellulose dispersion is diluted with a liquid from the initial concentration (concentration of the product from the manufacturing process) to a suitable initial concentration to ensure that it is coated on or distributed into the gauze. Depending on the characteristic viscosity of the nanofibrillar cellulose grade, the initial concentration may be lower or higher, and it may be in the range of 0.1-10%. Higher concentrations may be used for low-viscosity grades, which may be spread uniformly on the filter fabric despite the high concentration. The nanofibrillar cellulose issues as aqueous nanofibrillar cellulose from a manufacturing process where the fibrous starting material suspended in water is disintegrated. Draining of the liquid out of the nanofibrillar cellulose dispersion may be called "dewatering" in the case of water or aqueous solution.

Auxiliary agents for enhancing the manufacturing process or improving or adjusting the properties of the product may be included in the nanofibrillar cellulose dispersion. Such auxiliary agents may be soluble in the liquid phase of the dispersion, they may form an emulsion or they may be solid. Auxiliary agents may be added already during the manufacturing of the nanofibrillar cellulose dispersion to the raw material or they may be added to a formed nanofibrillar cellulose dispersion. The auxiliary agents may be also added to the final product, for example by impregnating, spraying, dipping or the like method. The auxiliary agents are usually not covalently bound to the nanofibrillar cellulose, so they may be releasable from the nanocellulose matrix. A controlled and/or sustained release of such agents may be obtained when using NFC as matrix. Examples of auxiliary agents include therapeutic (pharmaceutic) and cosmetic agents and other agents affecting to the properties of the product or to the properties of the active agents, such as surfactants, plasticizers, emulsifiers or the like. In one embodiment the dispersion contains one or more salts, which may be added to enhance the properties of the final product or to facilitate water removal from the product in the manufacturing process. One example of the salt is sodium chloride. The salt may be included in an amount in the range of 0.01-1.0% (w/w) of the dry matter in the dispersion. The final product may also be dipped or soaked in a solution of sodium chloride, such as in an aqueous solution of about 0.9% sodium chloride. Desired sodium chloride content in the final product may be in the range of 0.5-1%, such as about 0.9%, of the volume of the wet product.

One example of the auxiliary agents include cofactors, or precursors of such cofactors, which have an effect to the activity of the bioactive molecule, such as enzyme cofactors. A cofactor may be a non-protein chemical compound, such as organic molecule, or inorganic ion, such as metallic ion, or a salt thereof. Organic cofactors may be divided into coenzymes and prosthetic groups. According to one definition a cofactor is an additional substance apart from protein and substrate that is required for enzyme activity, and a prosthetic group as a substance that undergoes its whole catalytic cycle attached to a single enzyme molecule. Examples of organic cofactors, or precursors thereof, include vitamins, such as B1, B2, B6, B12, niacin, folic acid, K, C; and non-vitamins, such as adenoside triphosphate, S-adenosyl methionine, coenzymes B, M and Q, cytidine triphosphate, glutathione, heme, lipoamide, methanofuran, molybdopterin, nucleotide sugars, 2'-phosphoadenosine-5'-phosphosulphate, pyrroloquinoline quinone, tetrahydrobiopterin, and tetrahydromethanopterin. Inorganic ions may be for example mono or divalent metal ions, such as metal cofactors, for example Fe, Co, Ni, Mg, Cu, Mn, or iron-sulfur clusters. Metal ions or salts thereof, such as cobalt chloride or magnesium chloride, may be required for metalloenzymes as bioactive molecules. The cofactors may be released from the NFC matrix, especially when the matrix is placed onto the target tissue. Therefore it is possible to obtain a medical product comprising one or more immobilized bioactive molecule(s) and one or more releasable auxiliary agent(s). This helps maintaining the optimal conditions for bioactivity and/or at between the NFC and tissue.

Hydrogels

In the medical products, if the nanofibrillar cellulose is not completely dewatered, it may have a moisture content in the range of 80-99.9% (w/w), or 50-99.8% (w/w). In one embodiment the nanofibrillar cellulose is present as a gel, preferably having a moisture content in the range of 90-99.8% (w/w).

One embodiment provides nanofibrillar cellulose in gel form, more particularly as a medical hydrogel. The gel may be mouldable and it may be applied onto an area requiring treatment, whereto it is attached.

The hydrogel may have a viscosity in the range of 2500-9000 Pa·s at and a water retention value in the range of 30-100 g/g. In one example the hydrogel has a viscosity in the range of 3000-8000 Pa·s. In one example the hydrogel has a viscosity in the range of 4000-7000 Pa·s, These viscosities are measured at the concentration of the hydrogel as provided, i.e. "at own concentration", which may be in the range of 4-8% (w/w), such as 4.1-8% (w/w), 4.5-8% (w/w), 5-8% (w/w), 5-7% (w/w), or 6-7% (w/w). Such solids content is relatively high for a nanofibrillar material, which in general forms a gel at very low concentrations. However, the high solids content was found to provide advantageous properties for the medical uses. The viscosities at own concentration may be measured with any suitable viscometer, and are different from Brookfield viscosity. In the tests the viscosities were measured with HAAKE Viscotester iQ Rheometer (Thermo Fisher Scientific, Karlsruhe, Germany) equipped with a Peltier system for temperature control.

In one example the hydrogel has a water retention value in the range of 30-60 g/g. In one example the hydrogel has a water retention value in the range of 40-50 g/g. The "g/g" refers to grams of water to a gram of hydrogel. Therefore the nanofibrillar hydrogel may contain up to 100 grams of water per one gram of dry hydrogel, which is generally not possible for conventional gel forming materials. The tested gels had water retention value in the range of 40-50 g/g which was found to provide advantageous properties for the intended purposes. Especially the high water content of the gel provided such toughness for the gel that it could be handled, moulded and for example detached from a wound without breaking the gel. The water retention was measured with AAGWR water retention method (Abo Akademi Gravitometric Water Retention), which is a coating colour static water retention method useful for nanofibrillar cellulose. In general conventional water retention measuring methods cannot be used for nanofibrillar cellulose having such high water content.

In one example the hydrogel has a viscosity in the range of 3000-8000 Pa·s, and a water retention value in the range of 30-100 g/g. In one example the hydrogel has a viscosity in the range of 4000-7000 Pa·s and a water retention value in the range of 30-100 g/g. In one example the hydrogel has a viscosity in the range of 2500-9000 Pa·s and a water retention value in the range of 30-60 g/g. In one example the hydrogel has a viscosity in the range of 3000-8000 Pa·s, and a water retention value in the range of 30-60 g/g. In one example the hydrogel has a viscosity in the range of 4000-7000 Pa·s and a water retention value in the range of 30-60 g/g. In one example the hydrogel has a viscosity in the range of 2500-9000 Pa·s and a water retention value in the range of 40-50 g/g. In one example the hydrogel has a viscosity in the range of 3000-8000 Pa·s, and a water retention value in the range of 40-50 g/g. In one example the hydrogel has a viscosity in the range of 4000-7000 Pa·s and a water retention value in the range of 40-50 g/g.

In one example the hydrogel has a compression work in the range of 15-60 J/m$^2$. Such a compression work was found to provide a tough hydrogel which was not prone to chip or break when handled. The hydrogel could be detached from a wound or a skin as substantially intact. In one embodiment the hydrogel has a compression work in the range of 20-55 J/m$^2$. In one embodiment the hydrogel has a compression work in the range of 25-55 J/m$^2$. In one embodiment the hydrogel has a compression work in the range of 25-40 J/m$^2$. The compression work may be calculated from measurements made with a texture analyser.

One example provides a method for preparing such a medical hydrogel, the method comprising providing pulp, disintegrating the pulp until nanofibrillar cellulose is obtained, forming the nanofibrillar cellulose into a hydrogel, wherein the hydrogel has a viscosity in the range of 2500-9000 Pa·s, such as 3000-8000 Pa·s, for example 4000-7000 Pa·s, and a water retention value in the range of 30-100 g/g, such as 30-60 g/g, preferably 40-50 g/g. The method may comprise immobilizing, such as covalently bonding, the bioactive molecule to the final nanofibrillar cellulose hydrogel after it is formed.

The nanofibrillar cellulose can be fibrillated into a desired fibrillation degree and it forms a gel having desired properties as described herein. In one example the nanofibrillar cellulose in the medical hydrogel is anionically modified nanofibrillar cellulose.

The hydrogel to be used as a medical hydrogel needs to be homogenous. Therefore the method for preparing the medical hydrogel may include homogenizing a hydrogel comprising nanofibrillar cellulose, preferably with a homogenizing device such as ones described herein. With this preferably non-fibrillating homogenizing step it is possible to remove areas of discontinuity from the gel. A homogenous gel having better properties for the medical applications is obtained. The hydrogel may be further sterilized, for example by using heat and/or radiation, and/or by adding sterilizing agents, such as antimicrobials.

Certain advantageous properties of the hydrogel comprising nanofibrillar cellulose include flexibility, elasticity and remouldability. As the hydrogel contains a lot of water, it also shows good diffusion and release properties of molecules. These properties are useful for example when the hydrogel is used as a cover for healing wounds, or in other medical applications, such as for delivering therapeutic or cosmetic agents.

Solidity refers to a property which gives the hydrogel an ability to resist breaking or chipping. The solidity may be evaluated for example by the compression work of the gel, which may be also called as toughness.

Toughness is a feature which also affects to other properties of the hydrogel, such as the removability. The compression work correlates to the toughness of the gel. With high compression work the hydrogel is not prone to chip or break when handled, for example detached from a wound or a skin as intact as possible. Another feature affecting to the removability or the detachability is the high water retention value. A hydrogel containing a high amount of water is stable and mouldable.

The stickiness of the hydrogel is low, especially with gels with high concentration over 4% (w/w) or more. Low stickiness is desired, so that the gel will not stick to the user's skin when applying the gel to a target. One feature which may correlate with low stickiness is water retention value. In general, the higher the water retention value, the less sticky the gel is. High water retention is desired because in such case the cohesion between the water molecules and the nanofibers in high.

Also the viscosity of the hydrogel, as provided i.e. at its own concentration, was found to have an effect to the mouldability, removability and stickiness of the product. If the viscosity is too low the hydrogel tends to be sticky. On the other hand, if the viscosity is too high the gel tends to chip or break.

Layered Products

One embodiment provides at least one layer comprising nanofibrillar cellulose and optionally other ingredients, such as non-nanofibrillar pulp or therapeutic or cosmetic agents or other auxiliary agents. The cellulose layer comprising nanofibrillar cellulose may be called herein also for example as a "layer", a "layer of membrane", a "membrane", a "layer comprising nanofibrillar cellulose" or a "membrane comprising nanofibrillar cellulose".

In general said layers or membranes may be prepared by providing a dispersion comprising nanofibrillar cellulose, and drying or dewatering said dispersion on a support. The support may include a filter or a filter may be provided in addition to the support, wherein the dewatering is carried out through the filter, which retains the nanofibrillar cellulose but allows water to pass. As a result a dried layer comprising nanofibrillar cellulose is obtained having a moisture content in the range of 0-20% (w/w), for example 1-10% (w/w). In general the moisture content may be affected by the ambient atmosphere and in many cases it is therefore in the range of 5-7% (w/w).

The dewatering may be carried out by applying vacuum through the filter, or by applying pressure to the layers, either from one or from two (opposite) sides, or by applying heat, or by a combination thereof.

In one embodiment the nanofibrillar cellulose is present as a layer, preferably having a moisture content in the range of 0-10% (w/w), such as in the range of 1-10% (w/w), for example in the range of 5-7% (w/w). The grammage of such layer of nanofibrillar cellulose may be in the range of 50-110 g/m$^2$, such as 60-100 g/m$^2$. These values are especially suitable for anionic grades. A layer may comprise substantially only nanofibrillated cellulose, such as 90-100%, 95-100%, 98-100%, 99-100% or 95-99%, 98-99% or 99-99.9% (w/w), or even about 100%, with only minor or trace amounts of other substances present. The layer comprising substantially only nanofibrillar cellulose may however contain one or more auxiliary agents as described herein. The nanofibrillar cellulose may be in such case the only cellulosic or fibrillar material in the layer.

The medical products may contain only one layer of nanofibrillar cellulose, or they may contain one or more additional layers, which may be nanofibrillar cellulosic layers and/or other layers. The nanofibrillar cellulose may be incorporated in a gauze, such as nonwoven. In one embodiment the medical product comprises a gauze, such as nonwoven. The gauze may be included or incorporated in the product in any suitable manner described herein. The moisture content of the combination may be in the same range as discussed in previous. In one example the nanofibrillar cellulose in a layer may have a moisture content in the range of 80-99.9% (w/w), or 50-99.8% (w/w), such as in the range of 90-99.8% (w/w), especially when incorporated with a gauze.

The layers or membranes comprising nanofibrillar cellulose may be used in multi-layered medical products. In one example the multi-layered medical products comprise at least a layer comprising nanofibrillar cellulose, and at least one layer of gauze. In one example the multi-layered products comprise at least two layers comprising nanofibrillar cellulose, and optionally at least one layer of gauze. In one example the multi-layered products comprise at least one gauze coated, either partly or completely, with nanofibrillar cellulose. The layers may be also laminated to each other.

One embodiment provides a medical product comprising
   a layer comprising nanofibrillar cellulose, preferably having a moisture content in the range of 0-20% (w/w), and comprising a bioactive molecule covalently bound to it, and
   a layer of gauze.

In one embodiment the medical product further comprises a second layer comprising nanofibrillar cellulose, such as wherein the layer of gauze is between a first layer comprising nanofibrillar cellulose and a second layer comprising nanofibrillar cellulose.

In one embodiment the method comprises providing a gauze, and incorporating the nanofibrillar cellulose to the gauze. Incorporating refers to any suitable method of combining the nanofibrillar cellulose and the gauze, such as coating, layering and/or laminating. A medical product comprising a gauze is obtained.

One example provides a method for preparing a medical product, said method comprising
   providing an aqueous dispersion of nanofibrillar cellulose,
   providing a layer of gauze,
   treating the layer of gauze with the aqueous dispersion of nanofibrillar cellulose, and
   dewatering the treated gauze,
to obtain the medical product. The method comprises immobilizing, such as covalently bonding, the bioactive molecule to the nanofibrillar cellulose, either before or after the dewatering.

The method comprises treating, such as coating, the layer of gauze with the aqueous dispersion of nanofibrillar cellulose. This may be carried out by providing the dispersion in a basin or the like and immersing or dipping the gauze into the dispersion. The gauze is kept in the dispersion for a time period suitable for letting the dispersion to treat or coat the gauze at least partially, and then the gauze is removed from the dispersion. Treating may refer to a process wherein a gauze is soaked with a dispersion comprising nanofibrillar cellulose. In practice usually the nanofibrillar cellulose does not penetrate the gauze in uniform manner but a more concentrated layer of nanofibrillar cellulose will be formed on the surface of the gauze in the final product. This process may be called coating. The nanofibrillar cellulose will bind the fibers of the gauze tightly and enhance its properties. Longer, especially non-shortened, nanofibrils may be preferred to enhance the binding. A concentrated zone or layer of nanofibrillar cellulose at a surface of the gauze enables maintaining the optimal conditions for treating the tissue specifically at the surface of the product. Less bioactive molecules are bound inside the product so the bioactive molecules are concentrated to areas where they can directly interact with the tissue, i.e. the bioactivity is provided mainly at the surface of the medical product. The inner part of the product may provide different conditions which may be helpful for example for permeability of the product.

Next the wet gauze may be pressed to remove excess dispersion and liquid, and to facilitate the penetration of the dispersion into the structure of the gauze. This facilitates the even distribution of the nanofibrillar cellulose in the gauze. The properties of the gauze may however have an effect to the penetration of the nanofibrillar cellulose into the gauze, for example in the case wherein the structure or the material of the gauze is different on different sides. In one example the method therefore comprises pressing the treated gauze, which may be carried out with any suitable pressing method and/or device, to obtain the medical product.

In one example the pressing is carried out in a nip, or more particularly in a nip roll. A nip refers to the contact area where two opposing rolls meet, such as in a press or calender. Nip rolls or pinch rolls may be powered rolls and they are usually used to press two or more sheets together to form a laminated product. In one example one roll is powered and the other one is freely movable. In the examples however they may be used to press the treated gauze so the obtained product is not a laminated product. The high pressure created at the nip point brings treated gauze into intimate contact, and can squeeze out any bubbles or blisters. Nip roller units can also be used as pullers for material being pulled off of rolls or being fed between operations. Nip rolls are sometimes called squeeze rolls, pinch rolls or even wringers. Nip rolls may be used in several arrangements, such as pond size press and size press. The nip rolls may be overlapping so that the freely movable roll on top forms the pressure against the gauze fed into the nip point. The nip rolls may be for example steel rolls, which may have fine grooving. Using nip rolls was found very effective for facilitating the penetration of the dispersion into the gauze and simultaneously removing excess dispersion from the gauze. Nip rolls are very useful in an industrial scale process, wherein a long gauze sheet is fed immediately from treatment to the nip rolls and further to a next step, such as to a dewatering step.

In one example the pressing is carried out in a pond press, more particularly a pond size press. In one example the pressing is carried out in a size press.

The treated gauze is finally dewatered. In one example the method comprises dewatering the pressed gauze. This is carried out after the pressing step, or if there are several treating and pressing steps, after the last pressing step.

The dewatering may be carried out by non-contact drying, such as with an infrared dryer, floating dryer or impingement dryer, or by contact drying, such as with a press dryer, cylinder dryer or belt dryer. Air impingement drying involves blowing hot air (such as at 300° C.) in gas burners at high velocity against the wet sheet. In belt drying, the product is dried in a drying chamber by contact with a continuous hot steel band which is heated either by steam or hot gas. The water from the band is evaporated due to the heat from the band.

When drying cylinder is used the surface of the product will be smooth and the drying is cost efficient. In one example the product is dewatered in a press dryer wherein the product is placed between a Teflon plate and a cloth or fabric, and also heat is applied.

The treatment, such as coating, and the dewatering may be done once, or the steps may be repeated, if necessary to maximize saturation and/or even distribution of the dispersion in the gauze. The steps of treating and dewatering, optionally with a pressing step in between, together may be called for example as an treatment run. A specific property, such as a grammage of the product, may be desired. In such case the treatment run is repeated until the medical product has reached the desired grammage. This may be applied to any other treatment. Therefore in one embodiment the treating and dewatering are repeated at least once, i.e. the treating and dewatering are carried out at least twice. In one embodiment the treating and dewatering are carried out several times, such as 2-6 times, for example 2, 3, 4, 5 or 6 times, or more. In one embodiment the treating and dewatering are repeated until the medical product has reached a grammage in the range of 25-80 $g/m^2$, such as 30-70 $g/m^2$, for example 35-65 $g/m^2$, or any other grammage disclosed herein. In one example such medical product has a grammage in the range of 45-63 $g/m^2$. In tests medical products obtained with this method with 4-5 treatment runs had grammages in the range of 47-55 $g/m^2$. The grammage may be also called as square mass.

The gauze as used herein refers to any suitable gauze, such as a fabric, a cloth or the like material comprising fibers. The gauze may be woven or nonwoven, sterile or nonsterile, plain or coated, or fenestrated (perforated or with slits), or a combination thereof. The gauze may be provided as a gauze sheet or fabric or the like.

In one example the gauze is woven. By one definition a woven gauze is a thin, translucent fabric with a loose open weave. In technical terms a woven gauze is a weave structure in which the weft yarns are arranged in pairs and are crossed before and after each warp yarn keeping the weft firmly in place. The gauze may comprise natural fibers, semi-synthetic fibers or synthetic fibers, such as viscose, rayon, polypropylene, polyester and the like, or combinations thereof, for example a viscose-polyester mixture or a mixture of cellulose (pulp) and polypropylene and/or polyester. When used as a medical dressing, gauze may be made of cotton. The gauze may also act as a pad of a patch. In one example the gauze is viscose-polyester gauze, for example non-woven. Such a non-woven gauze is very porous and permeable and it is moderately elastic providing irreversible elongation in one direction.

Preferably the gauze is nonwoven. Nonwoven gauze comprises fibers pressed together to resemble a weave, which provides improved wicking and greater absorbent capacity. Compared to woven gauze, this type of gauze produces less lint and has the benefit of leaving fewer fibers behind in a wound when removed. Examples of nonwoven gauze dressings include gauzes made of polyester, viscose, or blends of these fibers which are stronger, bulkier, and softer than woven pads.

The gauze may comprise absorbing material, for example to enable the medical product to absorb exudate, to soak up blood, plasma, and other fluids exuded from the wound and containing them in one place. The gauze may also stem bleeding and to help sealing a wound. The gauze may also absorb a therapeutic agent or other agent.

In one example the gauze comprises natural fibers or natural-fiber-based material, such as cotton, cellulose, linen, silk or the like. Natural fibers provide free hydroxyl groups which helps attaching the gauze to the nanofibrillar cellulose via hydrogen bonds. Also semi-synthetic fibers may provide free hydroxyl groups, such as viscose.

In one example the gauze comprises natural gauze, such as cellulose or cotton gauze, synthetic gauze or semi-synthetic gauze, or a mixture thereof. In one example the gauze comprise a mixture of polypropylene and cellulose. In one example the gauze comprise a mixture of polypropylene, polyester and cellulose. In one example the gauze comprise a mixture of viscose and polypropylene. In one example the gauze comprise a mixture of viscose and polyester. Cellulose fibers may be mixed with these materials. These gauzes may be non-woven.

The gauze should be highly permeable allowing fluids to pass through. The gauze is not a filter and it does not limit the flow through of most macromolecules. The gauze may not be used as a filter for dewatering a dispersion comprising nanofibrillar cellulose. The gauze may be porous and/or it may be fenestrated having perforations or slits or the like. A paper or cardboard is not a gauze. More particularly paper may not be suitable as paper does not provide high enough tear strength in such grammages or thicknesses which may be desired for the multi-layer products. Paper generally has a shorter fiber length than a gauze. The same applies to cardboard or other similar cellulosic products. However, paper, cardboard or the like cellulosic materials may be suitable for some specific applications. In one example the gauze is non-cellulosic. The gauze may comprise long fibers having an average fiber length of at least 5 mm, at least 7 mm, or at least 10 mm, for example in an amount of at least 15% (w/w) of the total gauze, or at least 20% (w/w) or at least 25% (w/w).

In one example the gauze is resilient. Many natural, semi-synthetic or synthetic fibers are resilient. However, in one example the gauze is rigid providing non-resilient properties, for when it comprises cotton. The gauze may provide reinforcing properties, for example to enhance the tear strength of the multi-layer product.

Tear strength (tear resistance) is a measure of how well a material can withstand the effects of tearing. More specifically it measures how well a material resists the growth of any cuts when under tension. Tear resistance may be measured by the ASTM D 412 method (the same may be used to measure tensile strength, modulus and elongation). Also a tear index may be presented, wherein tear index=tear strength/grammage, and it is usually measured in $mNm^2/g$.

The gauze may have a tear strength in the range of 800-2000 mN. Tear index may be measured with ISO 1974. The tensile strength of a gauze may be for example in the range of 0.6-1.5 kN/m, such as 0.7-1.2 kN/m. Tensile strength may be measured by ISO 1924-3. The gauze may have a grammage in the range of 20-60 $g/m^2$, for example in the range of 30-55 $g/m^2$. Grammage may be measured by ISO 536. The gauze may have a density for example in the range of 100-400 $g/cm^3$, such as in the range of 160-330 $g/cm^3$. Also a bulk may be presented as $cm^3/g$, measured by ISO 534.

A layer of gauze, such as a dry gauze, may have a thickness in the range of 100-1000 µm, such as 100-200 µm, 150-200 µm, 200-300 µm, 300-400 µm, 400-500 µm, 500-600 µm, 600-700 µm, 700-800 µm, 800-900 µm or 900-1000 µm. However, thicker gauzes may also be used, for example up to 2000 or 3000 µm. In one example the thickness of the gauze is in the range of 100-200 µm, such as 100-120 µm, 120-140 µm, or 140-160 µm or 160-190 µm.

The medical product may have a thickness in the range of 50-500 µm. In one example the medical product has a thickness in the range of 50-250 µm, such as 80-200 µm, or 100-150 µm, or 110-140 µm. Thickness may be measured as bulking thickness by ISO 534.

With a reinforcing gauze the tear strength of the medical structure is remarkably higher than in a product without the gauze. In one embodiment the medical product has a tear index in the range of 10-100 $mNm^2/g$. In one example the medical product has a tear index in the range of 15-70 $mNm^2/g$. The tear strength may be different in one direction and in a perpendicular direction, which may be affected by the properties of the gauze. For example a gauze may have different properties to the perpendicular directions, which may be called as machine direction (md) and cross direction (cd).

In one example the medical product comprising the gauze has a grammage in the range of 25-80 $g/m^2$. In one example the medical product has a grammage in the range of 30-70 $g/m^2$. In one example the medical product has a grammage in the range of 35-65 $g/m^2$. In one example the medical product has a grammage in the range of 45-63 $g/m^2$. Such products contained an effective amount of nanofibrillar cellulose, but also exhibited other desirable properties, such as desired air and/or liquid permeability, tear strength, and/or other properties discussed herein which are desired for medical products.

The grammage of the nanofibrillar cellulose in the medical product comprising the gauze may be in the range of 1-50 $g/m^2$, for example 1-20 $g/m^2$, such as 2-20 $g/m^2$, 2-12 $g/m^2$ or 5-15 $g/m^2$, measured as dry weight of the product.

In one example the medical product comprising the gauze has a density in the range of 300-700 $g/cm^3$, such as 350-530 $kg/m^3$. The density may be measured as apparent bulking density by ISO 534.

The air permeance, also called as air permeability, of the medical product comprising the gauze, preferably as autoclaved, may be less than 120 ml/min, less than 300 ml/min, or less than 600 ml/min, such as less than 1000 ml/min or less than 2000 ml/min. The air permeance correlates in general with the amount of nanofibrillar cellulose. The higher the amount of nanofibrillar cellulose, the lower the air permeance. With an exemplary air permeance of less than 600 ml/min, or less than 500 ml/min the amount of nanocellulose is at suitable level for many applications. Air permeability may be measured by ISO 5636-3.

The medical products described herein, with or without the gauze, may be used in several applications. One specific field is medical applications, wherein the materials are applied on living tissue, such as skin. The structures may be used in medical products, such as patches, dressings, bandages, filters and the like. The medical products may also be therapeutic products, such as therapeutic patches containing medicament. In general the surface of the product comprising nanofibrillar cellulose will be in contact with the skin during the use. A surface of nanofibrillar cellulose may provide advantageous effects when it is in direct contact with the skin, for example it may promote healing of a wound or other damage on a skin, and simultaneously it provides the bioactive substances from the medical product to the skin.

The medical product comprising the gauze provides enhanced mechanical strength and other properties, such as high tear strength (tear resistance), especially at moist conditions. By combining a supporting and reinforcing structure, such as a dressing fabric, i.e. the gauze, with nanofibrillar cellulose an coated and/or layered product is formed. The fabric creates a continuous supporting network and the strength of the network is not significantly affected by moist conditions.

Certain advantageous properties of the medical products comprising the gauze include flexibility, elasticity and remouldability. If the nanofibrillar cellulose contains moisture, it may also show suitable permeability. These properties are useful for example when the product is used as a dressing for healing wounds, or in other medical applications, such as for delivering therapeutic or cosmetic agents.

Flexibility is a feature which is desired in many applications, such as in medical applications. Flexible patches and dressings comprising nanofibrillar cellulose are useful for applying onto skin, for example for covering wounds and other damages or injuries, such as burns.

The relatively low amount and the even distribution of the nanofibrillar cellulose in the product have effects to flexifibility, elasticity, remouldability and rigidity. The rigidity of the product is relatively low and the product has an open structure which provides suitable air and/or liquid permeability.

The flexibility or elasticity (elongation) of the product comprising the gauze can also be affected with the choice of the gauze. The nanofibrillar cellulose itself has a limited flexibility and elasticity, especially when dry. For this reason it is important to match the gauze and the network of nanofibrillar cellulose to obtain a balance between the elastic properties of gauze and nanofibrillar cellulose network.

The medical products comprising the gauze also provide high absorption capacity and absorption speed, which properties are desired in medical applications such as wound healing and the like. Large sheets may be prepared which may be used for covering large areas.

Immobilization of a Bioactive Molecule

It is possible to immobilize different kinds of substances to the nanofibrillar cellulose and/or to the medical products, such as layered products or gels, described herein.

Two strategies for loading compounds on the surfaces are irreversible immobilization and reversible immobilization. The most promising approach is the irreversible immobilization due to lack of release of undesirable compounds during the time. The irreversible immobilization of bioactive proteins and enzymes on nanocellulose has many advantages with respect to inorganic nanoparticles such as biocompatibility and extremely low environmental impact. Additionally, enzymes possess activities that inorganic compounds are unable to exhibit and this is crucial for several biomedical applications. Examples of irreversible methods include covalent bonding, such as through primary amines or crosslinking using carbodiimide, and entrapment.

In general, a method for preparing a medical product comprises
   providing nanofibrillar cellulose,
   providing one or more bioactive molecule(s), and
   immobilizing the bioactive molecule(s) to the nanofibrillar cellulose.

In one embodiment the immobilizing comprises covalent bonding. The covalent bonding may be carried out by using any suitable method of forming a covalent bond between the bioactive molecule and the nanofibrillar cellulose. Covalent bonding includes covalent crosslinking. It is also possible to use a linker molecule between these two, such as a nucleotide linker or a peptide linker, an anchor group or a cantilever.

The immobilization may comprise crosslinking, such as covalent crosslinking or non-covalent crosslinking. Covalent crosslinking is preferred. According to one definition, a cross-link is a bond that links one polymer chain to another. One or more crosslinking agent may be provided to obtain covalent crosslinking, or the crosslinking may be obtained by UV radiation. The crosslinking may be carried out by using carbodiimide.

The immobilization may also comprise entrapment. The entrapment may be carried out on beads or bres or by microencapsulation.

One embodiment provides a method for preparing a medical product, the method comprising
   providing nanofibrillar cellulose,
   providing one or more bioactive molecule(s), and
   covalently bonding the bioactive molecule(s) to the nanofibrillar cellulose.

One embodiment provides a method for preparing a medical product, the method comprising
   providing nanofibrillar cellulose,
   providing one or more bioactive molecule(s), and
   crosslinking the bioactive molecule(s) to the nanofibrillar cellulose.

The nanofibrillar cellulose may be any nanofibrillar cellulose described herein and it may be provided at any suitable dry matter content and/or form. In one example the nanofibrillar cellulose is homogenized before the covalent bonding, for example for 1-5 minutes with a blade type homogenizer or the like, such as at 10000-20000 rpm, to render the material more reactive for covalent bonding.

Certain agents may be used to obtain the covalent bond between the bioactive molecule and the nanofibrillar cellulose. One example of such agent includes carbodiimides.

EDC (or EDAC; 1-ethyl-3-(3-dimethylaminopropyl)carbodiimide hydrochloride) (N-(3-dimethylaminopropyl)-N'-ethylcarbodiimide hydro-chloride) is a suitable carbodiimide for conjugating biological substances containing carboxylic groups or carboxylates and amines.

The main advantage of EDC relies in its water-soluble nature, which allows for its direct addition to a reaction and there is no need to dissolve it in organic solvents. The products that mainly originate from the reaction may be removed by simple multiple rinsing, gel filtration or dialysis because they are water-soluble compounds.

Sulfo-NHS provides a more stable reaction pathway with the introduction of a amine-reactive sulfo-NHS ester. The EDC alone is not enough to provide the formation of a conjugate that is stable for enough time to react with a primary amine. It was reported that the stability of O-acylisourea intermediates is seconds in length. FIG. 1 shows an immobilization scheme of acylase with EDC and sulfo-NHS.

Nanocellulose contains reactive carboxylic groups that may be converted to NHS esters using EDC and sulfo-NHS activation. The reactive groups are able to interact preferentially with a primary amine of a protein and the conjugate is formed in two hours after the activation reaction. This chemistry may be used to immobilize a protein, for example an acylase protein, on nanocellulose membrane, that carries the carboxylic group. The amide bond that is formed is stable, and a variety of chemical conjugates may be formed using EDC provided one of the molecules contains an amine and the other a carboxyl group.

Other nucleophiles are also reactive and particular attention has to be given to this aspect. Sulfhydryl groups may attack the active species and form unstable thiol ester linkages. Oxygen atoms may act as the attacking nucleophile, such as those in water molecules. An ester intermediate is generally unstable in water, with the result that the activated surface with EDC and Sulfo-NHS may be restored to the initial carboxylic group with expulsion of isourea.

EDC reacts with carboxylic acid groups to form an active O-acylisourea intermediate that is easily displaced by nucleophilic attack from primary amino groups in the reaction mixture. The primary amine forms an amide bond with the original carboxyl group, and an EDC by-product is released as a soluble urea derivative. The EDC crosslinking is most efficient in acidic conditions, such as at a pH of 3-6, for example about 4.5. It is preferably carried out in a buffer which does not contain extraneous carboxyls and/or amines, such as MES buffer (4-morpholinoethanesulfonic acid). The reaction may be also carried out in phosphate buffers and neutral pH up to 7.2. The efficiency of such reaction is lower but the conditions are compatible with the reaction chemistry. The amount of EDC can be increased to compensate for the reduced efficiency.

EDC can be also used for activating phosphate groups in the presence of imidazole for conjugation to primary amines. This may be used to crosslink or immobilize oligonucleotides through their 5' phosphate groups.

Another carbodiimide crosslinker is dicyclohexyl carbodiimide (DCC), which is able to crosslink carboxylic acids to primary amines in the same manner as EDC. However DCC is not water-soluble, and it is therefore not suitable for all types of products.

In one embodiment the immobilization, such as covalent bonding, is carried out in an aqueous medium. Also other manufacturing steps may be carried out in aqueous medium. This is advantageous for both the bioactive molecules and to the nanofibrillar cellulose, which may be damaged or their activity, structure and/or properties may be altered in organic solvents. For example the NFC might be agglomerated and fiber or fibril bundles might be formed so that the homogenous nanostructure would be disturbed and the material would lose its advantageous properties. This can be detected from the final product for example microscopically. If the reactions would we carried out in organic solvent, it would be necessary to exchange the solvent back to aqueous one.

Proteins can be immobilized or crosslinked via primary amines or sulfhydryl groups rather than through carboxylic groups. On the other hand, peptides and other small carboxyl-containing molecules can be immobilized using EDC to polymerize and conjugate them to an amine-derivatized surface material.

In one embodiment the covalent bonding is carried out through primary amines. In one embodiment the covalent bonding is carried out through sulfhydryl groups, which are also called thiols. The primary amines or sulfhydryl groups may be in the bioactive molecule. The covalent boding to nanofibrillar cellulose may be through carboxylic groups in the nanofibrillar cellulose, or in hemicellulose included in the fibrillated material.

Sulfhydryls exist in proteins in the side-chain of cysteine amino acids. Pairs of cysteine sulfhydryl groups are often linked by disulfide bonds (—S—S—) within or between polypeptide chains as the basis of native tertiary or quaternary protein structure. In general, only free or reduced sulfhydryl groups (—SH) are available for reaction with thiol-reactive compounds.

Sulfhydryls are present in most proteins but are not as numerous as primary amines; thus, crosslinking via sulfhydryl groups is more selective and precise. Sulfhydryl groups in proteins are often involved in disulfide bonds, so crosslinking at these sites typically does not significantly modify the underlying protein structure or block binding sites. The number of available sulfhydryl groups can be easily controlled or modified. For example they can be generated by reduction of native disulfide bonds, or they can be introduced into molecules through reaction with primary amines using sulfhydryl-addition reagents, such as 2-iminothiolane (Traut's Reagent), SATA, SATP, or SAT(PEG)4. Finally, combining sulfhydryl-reactive groups with amine-reactive groups to make heterobifunctional crosslinkers provides greater flexibility and control over crosslinking procedures.

Sulfhydryl-reactive chemical groups include haloacetyls, maleimides, aziridines, acryloyls, arylating agents, vinylsulfones, pyridyl disulfides, TNB-thiols and disulfide reducing agents. Most of these groups conjugate to sulfhydryls by either alkylation (usually the formation of a thioether bond) or disulfide exchange (formation of a disulfide bond).

The "bioactive molecule" as discussed herein may comprise one or more different bioactive molecules. The bioactive molecule(s) may be selected from enzymes, proteins, nucleic acids, hormones, cytokines, photosensitizing molecules, anti-cancer drugs and the like. Proteins, including polypeptides which contain less than 20-30 residues, include a variety of bioactive molecules, such as enzymes, and proteins having a function in cell signalling, immune response, cell adhesion, cell cycle, ligand binding or the like. A protein may contain one or more domains, which may be similar or different.

In one embodiment the bioactive molecule is an enzyme, such as a protein enzyme. Protein enzymes may be immobilized covalently with the methods described herein, preferably in an aqueous environment. Proteins covalently bound to nanofibrillar cellulose will maintain their activity and stability, which may be even improved by the immobilization.

In one embodiment the bioactive molecule is a quorum quenching protein, which is an enzyme, such as an acylase, an amidase, an amylase, Subtilisin A, a lactonase, or an oxidoreductase. These belong to hydrolases, which are enzymes that catalyse the hydrolysis of a chemical bond. Therefore in one example the bioactive molecule is a hydrolase, which may be able to hydrolase one of the following: ester bonds, sugars, ether bonds, peptide bonds, carbon-nitrogen bonds, acid anhydrides, carbon-carbon bonds, halide bonds, phosphorus-nitrogen bonds, sulphur-nitrogen bonds, carbon-phosphorus bonds, sulfur-sulfur bonds, or carbon-sulfur bonds. Examples of hydrolases include acylase, amidase, amylase, esterase, nuclease, phosphodiesterase, lipase, phosphatase, DNA glycosylase, glycoside hydrolase, protease, peptidase, acid anhydride hydrolase.

One example of an acylase is Acylase I from *Aspergillus melleus*, which may be also called as aminoacylase I. Aminoacylase (EC 3.5.1.14) is an enzyme that catalyzes the chemical reaction: N-acyl-L-amino acid+$H_2O \leftrightarrow$carboxylate+L-amino acid. It belongs to the family of hydrolases acting on carbon-nitrogen bonds other than peptide bonds, specifically in linear amides. Acylase I participates in urea cycle and metabolism of amino groups.

One example of an amidase is Penicillin amidase, such as one from *Escherichia coli*. A penicillin amidase (EC 3.5.1.11) is an enzyme that catalyzes the chemical reaction penicillin+$H_2O \leftrightarrows$a carboxylate+6-aminopenicillanate. It belongs to the family of hydrolases acting on carbon-nitrogen bonds other than peptide bonds, specifically in linear amides. The systematic name of this enzyme class is penicillin amidohydrolase.

An amylase is an enzyme that catalyses the hydrolysis of starch into sugars. Specific amylase proteins are designated by $\alpha$, $\beta$ and $\gamma$. All amylases are glycoside hydrolases and act on $\alpha$-1,4-glycosidic bonds.

Subtilisin is a non-specific protease initially obtained from *Bacillus subtilis*. Subtilisin A is a member of the Serine S8 Endoproteinase family. It has broad specificity with a preference for a large uncharged residue in the P1 position. It hydrolyzes native and denatured proteins, and is active under alkaline conditions.

A photosensitizing molecule, also called as a photosensitizer, is a molecule which may be used in photodynamic therapy (PDT). PDT is a form of phototherapy involving light and a photosensitizing chemical substance, used in conjunction with molecular oxygen to elicit cell death (phototoxicity). PDT applications involve a photosensitizer, a light source and tissue oxygen. The wavelength of the light source needs to be appropriate for exciting the photosensitizer to produce radicals and/or reactive oxygen species. PDT can be used to kill microbial cells, including bacteria, fungi and viruses, and it may be also used for treating cancer. One example of such cancer is melanoma, which is further divided into three types of cancer: basal cell, squamous cell and melanoma. Basal cell and squamous cell cancers are the most common types of skin cancer, but they are less deadly and more readily treated than melanoma.

PDT may be use for treating numerous other health related conditions. For example, PDT may be used for treating immunological effects (new antibiotics), inflammation and bacterial infections. PDT activates and suppresses the immune system, by a combination of effects that begins after the light treatment. In cancer treatment the curative properties arise from the death of the irradiated cancer cells. The damage to the plasma membrane and membrane of the cellular organelles by singlet oxygen can trigger other events with far reaching consequences. PDT may be also used for treating dental infections, nasal infections, wounds, ulcers and the like.

Another PDT-induced effect is inflammation. Vascular destruction, observed after PDT, is similar to the inflammatory response after tissue injury or bacterial infection. Typical for this process is the release of a wide range of potent mediators including vasoactive substances, components of clotting cascades, proteinases, peroxidases, radicals, leucocytes, chemo attractants, cytokines, growth factors, and other immune regulators.

If auxiliary agent(s) are to be incorporated in the medical products, they may be included before or after immobilizing the bioactive molecule. However, especially organic molecules, such as cofactors, or other substances which are meant to be released from the nanocellulose matrix, are preferably incorporated after immobilizing the bioactive molecule, especially by covalent bonding.

In one embodiment the method comprises adjusting the moisture content of the nanofibrillar cellulose to the range of 0-20% (w/w), or to 0-10% (w/w), such as to the range of 1-10% (w/w), for example to the range of 5-7% (w/w). This may be done before or after the immobilization. Such nanofibrillar cellulose is in practice substantially dry, and may enhance the storage stability of the product. However, when applied to the target the product will absorb water and the moisture content will rise.

In one embodiment the method comprises adjusting the moisture content of the nanofibrillar cellulose to the range of 50-99.8% (w/w), such as to the range of 90-99.8% (w/w). This may be done before or after the immobilization. Such nanofibrillar cellulose may be mouldable, or it may be in a gel form.

The present application provides a medical product comprising a bioactive molecule immobilized to nanofibrillar cellulose. The immobilization may be any of the immobilization disclosed herein, such as reversible or irreversible immobilization, such as covalent immobilization or bonding, crosslinking, entrapments and the like.

One embodiment provides a medical product comprising a bioactive molecule covalently bound to nanofibrillar cellulose. One embodiment provides a medical product comprising a bioactive molecule crosslinked to nanofibrillar cellulose. One embodiment provides the medical product obtained with the method described herein.

One embodiment provides the medical product described herein packed in a separate packing. Separate packings may be provided as a series of packings. Usually such packed products are provided as sterilized. The medical products, such as layered products or gels, may be provided as unit dosages. An example of an unit dosage of a layered product is a strip. The layered product may be also provided as a sheet which may be cut to obtain a piece having desired size. An example of an unit dosage of gel is a piece of gel packed in an unit package. The gel may also be provided from a tube, can, jar or the like container. The unit dosages or other forms of the products may be provided as packed in sealed packages, such as sealed plastic packages, preferably as sterile.

One embodiment provides a kit comprising the medical product described herein, for example a packed product, wherein the kit may contain one or more of the packed products. The kit may also contain other materials or equipment, such as a container containing saline solution or the like for pretreating the product(s) prior to use.

The medical products described herein may be used in methods for treatment, such as methods for treating a subject, such as a human subject, by providing a medical products described herein, and applying the product onto a tissue of the subject. The treatment may further include moistening the medical product with aqueous solution, for example with water or buffer solution and/or solution containing one or more auxiliary agent(s) described herein, for example cofactor(s), inorganic ion(s) or salt(s) or the like agents, which may facilitate the function of the bioactive molecule and/or control the conditions at the site of treatment. The condition to be treated may be any condition described herein or other condition, which may be treated with the bioactive molecule immobilized to the medical product.

One example provides a method for suppressing and/or preventing bacterial biofilm formation, the method comprising applying the medical product described herein onto a subject comprising or suspected having or suffering from bacterial biofilm formation.

One example provides a method for treating skin wounds or other damages or injuries, the method comprising applying the medical product described herein onto the wound, damage, or injury. The term "wound" as used herein refers to any damages, injuries, diseases, disorders or the like on a tissue, such as skin, including open or closed wounds, wherein the healing of the wound is desired and may be promoted with the product described herein. The wound may be clean, contaminated, infected or colonized, and it may involve biofilm formation. Examples of open wounds include abrasions, avulsions, incisions, lacerations, puncture wounds and penetration wounds. Examples of closed wounds include hematomas, crush injuries, sewn wounds, grafts and any skin conditions, diseases or disorders. The wounds may be chronic. Examples of conditions, diseases or disorders of the skin include acne, infections, vesiculobullous diseases, cold sore, cutaneous candidiasis, cellulitis, dermatitis and eczema, herpes, hives, lupus, papulosquamous, urticaria and erythema, psoriasis, rosacea, radiation-related disorders, pigmentation, mucinoses keratosis, ulcer, atrophy, and necrobiosis, vasculitis, vitiligo, warts, neutrophilic and eosinophilic diseases, congenital, neoplasms and cancer, such as melanomas and tumours of epidermis or dermis, or other diseases or disorders of epidermis and dermis.

One specific example provides a method for treating skin wounds covered with a graft, such as a skin graft, for example a mesh graft or a full thickness graft, the method comprising applying the medical product described herein onto the graft.

Grafting refers to a surgical procedure to move tissue from one site to another on the body, or from another person, without bringing its own blood supply with it. Instead, a new blood supply grows in after it is placed. Autografts and isografts are usually not considered as foreign and, therefore, do not elicit rejection. Allografts and xenografts are recognized as foreign by the recipient and are rejected.

Skin grafting is often used to treat skin loss due to a wound, burn, infection, or surgery. In the case of damaged skin, it is removed, and new skin is grafted in its place. Skin grafting can reduce the course of treatment and hospitalization needed, and can also improve function and appearance. There are two types of skin grafts: Split-thickness skin grafts (epidermis+part of the dermis) and full-thickness skin grafts (epidermis+entire thickness of the dermis).

A mesh graft is a full- or partial-thickness sheet of skin that has been fenestrated to allow drainage and expansion. Mesh grafts are useful in many locations on the body because they conform to uneven surfaces. They can be placed in locations that have excessive motion because they can be sutured to the underlying wound bed. Additionally, their fenestrations provide outlets for fluid that may accumulate beneath the graft, which helps reduce tension and the risk of infection and improve vascularization of the graft.

It has been found out in clinical tests that the medical product attaches to a graft area and acts as a protective layer. As the graft heals, the product forms a scab-like structure together with the graft. The properties of the product comprising nanofibrillar cellulose promote the healing, and the medical product with the formed dry scab will come loose in similar way as a regular scab behaves in normal wound healing process.

Before applying the medical product onto skin the product may be pretreated i.e. moisture or wetted, in general with an aqueous solution. The moisturizing or wetting may be carried out for example by using water or regular physiological saline solution, which is usually a solution of 0.90% w/w of NaCl, having an osmolality of about 308 mOsm/l. Other types of aqueous solutions may also be used, such as saline solutions with different concentrations. Moisturizing or wetting the material enhances contact with the skin and the moldability of a sheet of material.

Next a specific application of the medical products for the prevention of bacterial biofilm formation though quorum quenching mechanism is described in detail and demonstrated by examples.

Bacterial Biofilm

One specific application of the medical products is prevention or suppression of bacterial biofilm formation.

In clinical settings, in case of chronic infections, biofilms are believed to play a crucial role. Some bacteria rely mainly on biofilm deposition in order to achieve high virulence and infect a host and in the case of S. aureus, S. epidermidis, and P. aeruginosa it is a major concern for the healthcare. Bacteria are able to build sessile communities on inert surfaces of medical devices, cells and tissues.

The presence of the biofilm is both a form of adaptation to the environment and a barrier from host defences. The bacteria within a biofilm are reportedly protected against antibodies, leukocytes, and antibiotics. In addition, biofilms may spawn systemic infections by sloughing of planktonic bacteria, leading to dissemination, bacteremia, sepsis, and death.

One basic definition of biofilm is "a structured community of bacterial cells enclosed in a self-produced polymeric matrix and adherent to an inert or living surface". The matrix components comprise proteins, nucleic acids, and exopolysaccharides that are believed to provide the cells with an array of advantages as compared to planktonic cells. This may be the reason behind the fact that it is estimated that about 60% of all microbial infections involve bacterial biofilms.

The different density among biofilm layers corresponds to the highly heterogeneous nature of the biofilm itself, because they comprise patches of cells that are interspersed in the EPS matrix. This creates open areas where water channels are formed, allowing nutrients to enter the lower layers of the biofilm and, in addition, allowing waste products to be removed. The bacteria found in a biofilm can either be of one species or it can, depending on the environment, comprise multiple species.

The biofilm is formed initially with the attachment of free-floating, planktonic microorganisms to a wound surface. This adhesion is reported to be weak and reversible, and an equilibrium is established. In case the bacteria are not removed from the tissue or surface, different mechanisms are involved to promote stronger adhesion. Cell adhesion structures, hydrophobicity of the material and the motivity of the bacteria are important parameters for the attachment. For example, some bacteria as P. aeruginosa exploit pili to anchor. Microorganisms depose extracellular matrix (ECM) and exopolysaccharides (EPS) to adjust hydrophobicity of the surface and increase the chances of aggregation. The EPS may also contain additional molecules metabolized from the environment, such as minerals and blood components. The resulting increased deposition of EPS and ECM, the recruitment of additional number of bacteria and a higher cell division determine the success and maturation of a biofilm.

The biofilm starts with the weak initial attachment and the final part consists in the detachment of bacteria and colonization of the host. The mature biofilm is hard to eradicate with traditional methods. It is weakly affected by antibiotic treatment since it consists in an additional pharmacokinetic barrier, difficult to cross for a small molecule as a chemotherapeutic.

As a matter of fact, bacteria within a biofilm are one thousand time more resistant to antibiotics than the corresponding free-floating planktonic colonies. When the final stage of biofilm deposition is completed, the biofilm itself is firmly attached to a surface.

Methods able to debris the biofilm act on mature biofilm, such as water treatment called hydrotherapy, and promote a physical detachment of bacteria from a surface (e.g. a wound). Hydrotherapy is not the unique treatment for the removal of biofilm. Shockwave therapy, ultrasound treatment, the utilization of cadexomar iodine, lactoferrin as a dissolving agent have the potential to promote biofilm detachment. Antibiotic treatment is usually associated to promote complete healing of the wound bed.

Current treatment guidelines recommend as first treatment of colonized wound is the repeated surgical debridement until the wound becomes self-sustaining. Additional therapies for the wound such as skin graft replacement have to be performed after the complete healing of the wound bed and any biofilm is detached. However, it is still difficult to remove biofilm from a tissue completely. In addition, complete wound healing is reported to be achieved 32-67%.

As discussed previously, the presence of the biofilm contributes to the antibiotic resistance of P. aeruginosa. It appears that the bacterium has an intrinsic resistance conferred by lowered permeability of the outer membrane as well as efflux pumps that rapidly shuttle many different compounds out of the cell.

Five different efflux systems have been identified in *P. aeruginosa*. The highly homologous efflux pump proteins consist of a cytoplasmic-membrane-associated drug proton antiport mechanism, a membrane channel-forming protein and a periplasmic fusion protein. The pumps have broad specificity and transport varying molecules, including dyes, detergents, antibiotics, organic solvents, and secondary metabolites and signalling molecules such as N-acyl homoserine lactone (AHLs). In addition, *P. aeruginosa* produce beta-lactamases encoded on the chromosome, conferring enhanced resistance to beta-lactam antibiotics. Other compounds also affected by the action of the pumps include heavy metals.

Generally, resistance to a drug or a heavy metal means that a bacterium can grow and form a culture or colony in the presence of that particular drug or heavy metal. Tolerance, on the other hand, refers to the situation in which a bacterial culture is not eradicated by treatments with that particular drug. Whether it is resistance or tolerance, both may contribute to the fact that the biofilm mode of growth enables the bacteria to survive the exposure to 1000-fold higher concentrations of a number of antibiotics compared with their growing counterparts. In other words, the underlying pathway responsible for biofilm resistance is multifactorial and usually it is difficult to discriminate between resistance and tolerance, since the molecular mechanisms behind the process are unknown. Restricted penetration of antimicrobial compounds into the biofilm accounts for some of the resistance. Because restricted penetration is based on bonding of the molecules to, most probably, the EPS matrix, it is believed that at some point, the matrix becomes saturated, and penetration will eventually occur without delay. On the other hand, EPS is probably constantly being produced, creating new spots for antimicrobial bonding.

Another factor adding greatly to biofilm tolerance is the very heterogeneous metabolic activity of the biofilm cells. In a biofilm, there exist gradients of nutrients and oxygen, which limit the growth rate of most of the cells (except for the cells on the surface of the film). Because antimicrobials mostly target metabolically active cells, the large slow growing parts of the biofilms are very difficult to target. Some antibiotics have reduced activity in oxygen-deprived environments, which also contributes to biofilm resistance as availability of oxygen is reduced in deeper levels of a biofilm. Another option is the expression of certain genes in a biofilm, conferring enhanced resistance to antibiotics. The exact nature of these genes remains to be elucidated.

Several factors are involved in the relationship between antibiotic resistance and the presence of the biofilm. First, as mentioned above, bacterial cells in biofilms produce a matrix of polysaccharide, which may retard or block antimicrobial agents from reaching the cell. In addition, it was found that 40% of the cell wall proteins in biofilm cells are different from those of planktonic cells; therefore, the permeability of the cell membrane may change, making it difficult for antimicrobials or immune factors to reach their targets.

Most antimicrobials inhibit growth-related cellular activities, such as protein, DNA, and cell wall synthesis. Hence, they are not efficient against biofilm cells that have slow or even no growth. Furthermore, the close cell-to-cell contact in biofilms provides a favorable environment for horizontal gene transfer, which results in easy spread of antimicrobial resistance.

Although several factors are responsible for antimicrobial resistance in biofilms, they are all related to the multicellular nature of biofilm communities because it has been shown that the biofilm cells lose their resistance rapidly after resuspension and planktonic growth.

*Pseudomonas aeruginosa* is among the most relevant pathogenic bacteria correlated to biofilm-associated cutaneous diseases. It is a gram-negative bacterium able to colonize wounds, known to rapidly develop resistance towards antibiotic-based therapies. For this reason there is increasing awareness of the peril of antibiotic resistance, while the development of innovative solutions able to counteract bacterial colonization of wounds emerges as crucial.

In vitro biofilm formation by *P. aeruginosa* has been studied. After initial attachment of *P. aeruginosa* to a surface, microcolonies are formed, which in turn can grow to larger structures with different shapes. To date, transcriptomic studies such as of *P. aeruginosa* biofilms have not a specific and unique set of genes that is expressed each time in order to depose the biofilm matrix. This finding strongly suggests that multiple pathways exist by which a biofilm can be built. Regardless, what is becoming evident is that bacterial cell-to-cell communication is required for a successful biofilm to form in vivo.

Biofilm deposition in pathogenic bacteria as *P. aeruginosa* is believed to be controlled through a tightly regulated and widely distributed bacterial communication system called quorum sensing. The production of small signalling molecules (autoinducers) as a response of the bacterial number in the environment strongly affects the virulence of bacterial colonies, such as biofilm assembly and toxin production. Interruption of this communication pathway is termed quorum quenching. This approach aims to neutralize autoinducer molecules.

Quorum Sensing

Bacterial species communicate through a mechanism known as quorum sensing (QS) to regulate and coordinate the gene expression that is important for virulence-factor production, including biofilm formation.

Examples of quorum sensing signal molecules include N-acyl homoserine lactone (AHL), N-(3-hydroxyacyl) homoserinelactone (3-hydroxy-AHL), N-(3-oxoacyl)-l-homoserine lactone (3-oxo-AHL), *V. harveyi* autoinducer-2 (AI-2), furanosyl borate ester form, *Pseudomonas* quinolone signal (PQS), 2-heptyl-3-hydroxy-4(1H)-quinolone, diffusible signalling factor (DSF), methyl dodecenoic acid, hydroxyl-palmitic acid methyl ester (PAME), and autoinducing peptide 1 (AIP-1) from *Staphylococcus aureus*.

Bacteria are able to sense the density of the surrounding bacterial population by quorum sensing. Bacteria are able to measure and respond to the concentration of signal molecules that derive from metabolism intermediates.

Gram-negative and Gram-positive bacteria are believed to use different signalling molecules to gather information from the environment, but there are some cases in which some general molecules are supposed to be used more broadly. The reason behind the production of signalling molecules relies on the fact that a single bacterial colony or multiple colonies need to cooperate in order to survive. For example, bacteria have been reported to use quorum sensing as a way to control virulence in order to infect the host, the higher is the number of bacteria, the higher chances of success are expected to be.

Bacteria grow until a certain amount of signalling molecule concentration is reached, and bacteria can act in concert and determine a specific action. In order to build up a sufficient concentration of QS molecules, diffusion barriers are required. A dense, mature biofilm is not completely independent from the environment, but diffusion is certainly lowered compared with the situation in a planktonic culture.

Gram-negative bacteria use N-acyl homoserine lactones (AHL), which are able to cross membranes and are detected by LuxR-type proteins that upon ligand bonding act as transcriptional activators of QS-controlled genes. QS signalling of Gram-positive bacteria mainly relies on small cyclic or linear peptides, which either are detected by a membrane-bound sensor kinase or imported directly as a result of a more complex mechanism that involves gene expression. The signalling molecule autoinducer-2 (AI-2) is thought to be a more general signal that has a role for the communication inter and intraspecies.

In addition, multiple QS systems can be integrated in one bacterial species as in *P. aeruginosa*. It uses a network that integrates N-3-oxododecanoylhomoserine lactone (3OC12-HSL)-dependent, N-butanoylhomoserine lactone (C4-HSL)-dependent, and 2-alkyl-4(1H)-quinolone-dependent QS circuits (the las, rhl, and pqs systems). The pqs system uses 2-heptyl-3-hydroxy-4(1H)-quinolone (the "*Pseudomonas* quinolone signal", PQS) as signal molecule. The las system controls the synthesis of the thiazole signal IQS. *P. aeruginosa* additionally uses pyoverdine and DSF-like unsaturated fatty acid signals to coordinate gene expression.

Virulence factors include biofilm deposition, toxin secretion, protease production and so on. Virulence factors mentioned above are able to interact negatively with the immune system of the host, causing immune complexes and phagocytic enzymes to be released, with the effect to cause extensive tissue destruction and inflammation.

The presence of the quorum sensing within bacterial colonies seems to have a tight connection with bacterial infections.

There are fundamental differences between antibiotics and quorum sensing inhibitors. The development of bacterial resistance is based on the fact that bacteria are able to organize quickly in order to overcome chemotherapeutics, that are small molecules. In case of inhibitors of quorum sensing, the development of an additional communication system based on different signalling molecules is a complex and time-consuming process, that will grant enough time for the treatment to be effective. Biofilms formed by quorum sensing mutants or biofilms treated with inhibitors of quorum sensing were found to be much more susceptible to the actions of antibiotics. This, in conjunction with the quorum sensing control of virulence factors, point out quorum sensing as a highly attractive target for chemotherapy against biofilm chronic infections.

Quorum Quenching

The strategies discussed herein aim to target quorum sensing molecules in order to disrupt the communication and furthermore to reduce bacterial virulence. Quorum quenching (QQ) refers to the ability of a specific compound to interfere with quorum sensing at some extent.

Quorum quenching enzymes cleave in a specific way the molecules of the quorum sensing communication. By competing with the production of quorum sensing signal molecules it is possible to lower the biofilm formation and the inflammation while triggering tissue repair. The anti-biofilm studies on quorum quenching have been mainly focused on the activity of quorum sensing inhibitors, small molecules able to interfere with bacterial communication. The utilization of small molecules for the treatment of wounds has several well-known drawbacks, that include the interaction with body compartments after entering systemic circulation, the considerably long drug development time and the fact that drugs of this type can be fairly good enzyme inhibitors, receptor ligands, or allosteric modulators.

Small molecules are able to target intracellular targets and have an effect on a transcriptional level, or with the interaction with a receptor involved in the quorum sensing. The utilization of enzymes to control quorum sensing aims to target extracellular signalling molecules in order to cleave them, with the effect to control and inhibit quorum sensing.

Compared with bactericidal or bacteriostatic strategies, quorum sensing interference is less likely to select for resistance, because it usually does not directly affect growth. Nature has evolved different tools to interfere with quorum sensing. Quorum quenching allows a prokaryotic or eukaryotic species to modulate the behavior of their microbial community and it consists in a naturally-occurring phenomenon. As in the case of the red macroalga *Delisea pulchra*, it produces halogenated furanones that show structural similarity to AHLs and act as quorum sensing inhibitors. Also eukaryotic hosts are able to interfere with quorum sensing. In fact, enzyme-catalyzed QQ strategy may be used widely.

In the case of Gram-positive *S. aureus*, which uses a quorum sensing peptide, enzymes that do not specifically target quorum sensing molecules have an effect on quorum sensing. Some enzymes are able to produce reactive oxygen and nitrogen species, with the effect of inactivating the peptide and promote the reduction of QS-related virulence.

Acylase from *Aspergillus melleus* is an example of a quorum quenching protein that was shown to efficiently interrupt bacterial signalling. Therefore it has the ability to control, delay and disrupt the biofilm deposition by pathogenic bacteria. Acylase was covalently immobilized to NFC by a cost-effective EDC/SNHS coupling synthesis that has the capability to be scaled up. Covalent attachment of enzymes may improve their stability and preserve enzymatic activity over the time.

In order to control biofilm deposition, the *P. aeruginosa* biofilm formation mechanism may be considered. Its biofilm development is controlled through the production of N-acyl homoserine lactone signalling molecules. Acylase is a remarkably cost-effective protein that irreversibly inactivates N-acyl homoserine lactone molecules (autoinducers). Acylase has the pivotal role to actively control *P. aeruginosa* biofilm deposition on catheters and other different medical-grade materials. Herein acylase was immobilized on nanocellulose membrane and the activity of the material was tested against *P. aeruginosa* PAO1, a bacterial strain isolated from a chronic wound.

The interaction of quorum quenching nanocellulose membrane and *P. aeruginosa* was further investigated. Biofilm deposition on the nanofiber matrix was estimated by Alamar Blue metabolic activity assay. Bacterial metabolic activity is believed to be directly proportional to the amount of biofilm deposited. Moreover, the amount of quorum sensing-regulated molecule pyocyanin was monitored. The reduced production of pyocyanin by *P. aeruginosa* PAO1 is an evidence of lowered quorum sensing communication efficacy and decreased expression of virulence factors.

The results show that quorum quenching nanocellulose membrane promotes the reduction of *P. aeruginosa* deposited biofilm and expression of virulence factors. The medical material prepared herein was shown to be effective after over 24 hours bacterial growth on the material at physiologically relevant temperature conditions (3rC) and physiological pH values. The present materials were able to disrupt biofilm deposition which is advantageous for wound healing purposes.

Quorum Sensing in Wound Healing

One of the most relevant issues of chronic wounds is the presence of the biofilm and the expression of virulence factors. Hence, conventional antibacterial compounds such as antibiotics lose their activity because of bacterial resistance. For the control of the bacterial colonization of wounds a new approach independent from the bacterial resistance is necessary. Bacteria are able to express signal molecules such as acyl-homoserine-lactone (AHL) and other compounds, as the result of a complex communication pathway called quorum sensing, widely described elsewhere. The quorum sensing signalling is known to affect the biofilm formation.

The principle of an enzyme-functionalized antivirulence device and mechanism of action is shortly the following. A) Commensal bacteria are naturally present on healthy skin and use signal molecules to communicate without being virulent. B) In case of wound, the bacteria have a favourable medium for their growth and start their colonization step. C) When bacterial concentration is over a certain threshold the bacteria adapt their behavior and start being virulent by reducing motility, synthesizing a biofilm and secreting virulence factors. D) Enzyme-containing devices hydrolyze as signal molecules and prevent infection by decreasing virulence factor secretion, biofilm synthesis and motility.

Hence, many molecules and enzymes were tested and found to be active against the quorum sensing signalling and are called quorum quenching compounds.

Simplified general scheme of a quorum sensing system of Gram-negative bacteria, and targets and strategies to interfere with QS includes a signal synthase (I), or a set of biosynthetic enzymes, which produce chemical signal molecules, which reach the extracellular environment by diffusion or transport. At high signal molecule concentrations, the signal receptor (R) forms a complex with the signal. The complex activates expression of the signal synthase gene(s) and directly or indirectly modulates the transcription of sets of target genes.

Several halogenated molecules such as furanone derivatives were tested and found to be active against bacterial structures that are able to trigger the quorum sensing signalling, but there are reports of bacterial resistance against these compounds.

For this reason quorum quenching enzymes represent a promising tool for the control of the bacterial population within the wound in that they are able to control biofilm formation and the expression of virulence factors by converting harmful signal molecules into inactive compounds. Three exemplary types of quorum quenching enzymes include AHL acylases, AHL lactonases and oxidoreductases active toward AHLs.

AHL lactonases catalyze the reaction that converts the AHL into a N-acyl homoserine derivative, which is able to re-circularize to the AHL at acidic pH. Conversely, the acylase reaction products cannot spontaneously regenerate a functional QS signal and the fatty acid generated by the acylase usually is readily metabolized. For the above reasons, AHL acylases are the most promising class of quorum quenching enzymes.

EXAMPLES

Materials and Methods
Handling of Bacterial Strains

*Pseudomonas aeruginosa* PAO1 DSM 22644 was purchased from DSMZ GmbH (Germany). The strain is isolated from an infected wound and used to study the development of biofilm under various conditions.

*E. coli* MG1655 was purchased from ATCC. The strain is not producing Pyocyanin pigment and is used as a control. Biosafety Class II Laminar used: Kojair biosafety cabinet class II Silver Line.

Preparation of Glycerol Stocks for Long-Term Storage

Cultures reconstituted from the reference stock should be used for preparing glycerol stocks for long-term storage as soon as possible after the reconstitution.

*Pseudomonas aeruginosa* PAO1 DSM 22644 reference stock was grown in 5 ml of TSB liquid media and incubated at +35-37° C. for 16-20 h. A certain amount of the suspension (1 ml) was dispensed into sterile cryovials containing 225 µl of sterile 80% glycerol per vial (final glycerol concentration 15%), and a vigorous mixing was performed. The vials were stored on −20° C. cool box immediately after adding the glycerol and finally transferred to −80° C. The viability of the stock was tested accordingly.

Preparation of Monthly Working Culture from a Glycerol Stock

Initiation of monthly working (MW) culture from a glycerol stock.

After placing any useful tool in a laminar air flow cabinet, the glycerol stock is moved from the −80° C. freezer and put on ice. An inoculum is scraped from the surface of the stock with a loop and streaked onto a TSA slant. The stock has to be immediately moved to the −80° C. freezer. The MW was marked with species data, strain number, MW mark, date and initials. The slant is incubated at +37° C. and transferred to +2-8° C. after 24 h. This procedure has to be repeated every month.

Preparation of Weekly Working Culture from a Glycerol Stock

Initiation of weekly working (WW) culture from a MW culture.

After placing any useful tool in a laminar air flow cabinet, the MW culture is moved from the +2° C. fridge. An inoculum is scraped from the surface of the stock with a loop and streaked onto a TSA slant. The WW was marked with species data, strain number, WW mark, date and initials. The slant is incubated at +37° C. and transferred to +2-8° C. after 24 h. This procedure has to be repeated every week. This WW culture is used for preparing inoculums for the antibacterial assay.

Preparation of Inoculums for Antibacterial Testing

Initiation of inoculums from a WW culture.

Day before the assay, a colony from the WW culture was inoculated into 5 ml of Tryptic Soy Broth and incubated at +37° C. with shaking at 200 rpm in an orbital incubator for minimum 16 and not more than 24 h. In case of *Pseudomonas aerugnosa* cultures, it was found useful to place an aluminium foil around the vial to prevent light to interfere with the production of pigments over the time.

Immobilization Reaction

Acylase from *Aspergillus melleus* (P. code 01818), >0.5 U/mg, was purchased from Sigma-Aldrich(Finland) as a quorum quenching protein.

N-(3-Dimethylaminopropyl)-N'-ethylcarbodiimide hydrochloride (EDC) and NHydroxysulfosuccinimide sodium salt (SNHS) were purchased from Sigma-Aldrich (Finland) as conjugating reagents.

MES Buffer was prepared using MES Monohydrate and MES sodium salt, both purchased from Sigma-Aldrich. MES Buffer Saline was prepared with the same approach as MES Buffer and sodium chloride was added at the final concentration of 150 mM.

HEPES Buffered Saline was prepared using 4-(2-hydroxyethyl)piperazine-1-ethanesulfonic acid (HEPES) purchased form Sigma-Aldrich.

Nanofibrillar cellulose obtained from wood was used in the tests. Nanofibrillar celluloses Lot 119671917t, Lot 11888 and Lot 11885 were provided by UPM-Kymmene (Finland). Lot 11888 and Lot 11885 are anionic nanofibrillar cellulose. Lot 119671917t is native nanofibrillar cellulose commercially available as Growdex®. The lots 11885 and 11888 are characterized in Table 1.

TABLE 1

| LOT | Solids content, % | Turbidity (HACH), NTU | Brookfield Viscosity at 10 rpm, 0.8%, mPa · s | Viscosity at own conc. shear rate 0.1 | Compression work J/m$^2$ "Toughness" | Water retention value g/g |
|---|---|---|---|---|---|---|
| 11885 | 3.8 | 21 | 5680 | 2190 | 15.5 | 47.0 |
| 11888 | 6.6 | 22 | 1080 | 6633 | 37.4 | 47.2 |

The rheological measurements were performed at 37° C. with HAAKE Viscotester iQ Rheometer (Thermo Fisher Scientific, Karlsruhe, Germany) equipped with a Peltier system for temperature control. Results were analyzed with HAAKE RheoWin 4.0 software (Thermo Fisher Scientific). Parallel 35 mm diameter steel plate-and-plate geometry was used with a 1 mm gap in all measurements. Before each measurement, the samples were allowed to rest for 5 min at 37° C. Controlled stress amplitude sweeps were performed to determine the linear viscoelastic region for different NFC hydrogel formulations. Constant angular frequency ω=1 Hz and oscillatory stress between 0.0001-500 Pa was used in all amplitude sweeps. The chosen oscillatory stresses for frequency sweeps were τ=50 Pa (3% NFC hydrogel), τ=80 Pa (5.7% NFC hydrogel) and τ=100 Pa (6.5% NFC hydrogel) and the angular frequency range was 0.6-125.7 rads$^{-1}$. Shear viscosity was measured by increasing the shear rate from 0.1 to 1000 1/s.

The settings used in the rheology measurements were as follows:
Amplitude: CS mode→linear viscoelastic region
shear stress amplitude sweep, 37° C., t=300 s hold→osc amp sweep, τ=0.0001-500 Pa, f=1 Hz (6.2832 rad/s) log, 16 steps
Frequency: CS mode
frequency sweep with constant shear stress, 37° C., t=300 s hold,
τ=50 Pa (3.2%), τ=80 Pa (5.7%) and τ=100 Pa (6.8%)
f=0.1-20 Hz (i.e. ω=0.6283 rad/s-125.7 rad/s)
log, 16 steps
Viscosity: CR mode
shear rate (1/s)=0.1-1000

The Preparation of the Nanocellulose Membrane.

The nanocellulose stock gel was diluted to the concentration of 1% with MQ water. The homogenization process of the nanocellulose was carried out using Polytron PT3000 blade-type homogenizer from Kinematica AG (Switzerland). The homogenization settings are: 15 k rpm and 3 minutes for each 30 ml of gel. The gel was gently shaken for 3 minutes and then left overnight in a suitable glass container. This simple process eliminated most of the bubbles created during the homogenization process. The homogenization process with Polytron may render the nanofibrils more reactive towards chemical modification.

Then, a selected amount of the anionic nanocellulose 1% gel (e.g. 48 ml) was distributed on a parafilm surface and the area was 6 cm×10 cm. The ideal concentration of anionic nanocellulose was chosen 8 mg/cm$^2$. An higher value provides a more concentrated, stronger membrane. The gel has to be dried overnight and an opaque, rigid film of nanocellulose is formed. The nanocellulose membranes are obtained using a metal hole punch. The membranes have a diameter of 6 mm. They are sterilized with dry autoclavation before use.

The Modification of the Nanocellulose Membrane.

EDC was stored at −20° C. while SNHS was stored at +4° C. EDC and SNHS are unstable compounds that react easily with water, so they were stored inside an appropriate container, under argon atmosphere and molecular sieves to avoid unwanted side reactions to occur. EDC and SNHS were equilibrated at room temperature completely before use. To increase reagent stability over the time, a stock of EDC was created and stored at −20° C. The stock was composed of several vials dried with molecular sieves for one week, the vials were weighted and EDC was added. With this approach, not all the EDC is thawed but a singular vial for a single use and then it may be easily disposed.

To start the immobilization reaction, a concentrated solution of EDC and SNHS was created by adding the required amount to a test tube. The addition of Milli-Q (MQ) water to the test tube has to be postponed until all the necessary tools and materials have been prepared under a laminar flow and sterile conditions. To obtain a concentrated solution of EDC and SNHS, MQ water was added accordingly. The tube was rapidly sterilized with a PVDF filter into another labeled test tube and vortexed prior the use. The chosen amount of EDC and SNHS from the stock was pipetted into each well of the 48-well plate containing the material to be modified (e.g. an anionic nanocellulose membrane) and an adequate amount of MES buffer at pH 6 in order to maintain the pH during the first reaction. The carboxylic acid moiety of the material to be modified is able to react with EDC and SNHS in order to obtain an amine-reactive NHS ester. The ester is reported to be generally stable in a water environment up to 6 hours at pH 6. The activation time is 15 minutes at 500 rpm with a multiwell shaker. The membranes in the 48-well plate were rinsed three times with 500 µl of sterile MES Buffer pH 6.

The protein solution was prepared in advance, dissolving a certain amount of acylase in a buffer saline solution. The buffer does not have to interfere with the immobilization reaction, MES buffer was chosen because it does not contain any reactive group that may interfere with the immobilization reaction. In case of choosing the buffer to dissolve the protein, additional care has to be given. The buffer not only has to avoid the presence of reactive chemical groups as SH, NH$_2$, etc, but also it has not to interfere with metal bonding: HEPES pH 8 and bicarbonate pH 8 are suitable. For example, phosphate buffered saline buffer is not suitable for the experiment because it may interact widely with the activity of metal enzymes (e.g. acylase) and it was not used for the immobilization reaction. After the formulation of the correct buffer carrier for the protein powder, a certain amount of protein solution was added to the 48-well plate containing the activated material after the washing process. The immobilization of the protein on the material requires at least two hours. After the immobilization reaction, the wells are rinsed three times with 500 µl of HEPES buffer at pH 8.

The Activity Test of the Immobilized Membranes.

The activity of the immobilized protein is tested with N-acetyl methionine solution 20 mM. N-acetyl methionine was purchased from Sigma-Aldrich. HEPES buffered saline contained 20 mM of HEPES, 20 mM of N-acetyl methionine, NaCl at the concentration 150 mM. N-acetyl methionine was dissolved in HEPES buffered saline pH 8 and the pH of the solution is adjusted to 8 with a pH-meter, since the addition of N-acetyl methionine determines a lower pH value. The N-acetyl methionine solution prepared was added to a 96-well plate containing the test membranes with the immobilized protein. The activity was monitored over 24 hours at 37° C. with shaking at 250 rpm using a multiwell shaker with heating function. The conditions were maintained to be the same that the membrane with protein encounters when incubated with *P. aeruginosa* culture. After 24 hours, a certain amount of the N-acetyl methionine solution was moved to a test tube and diluted 1:40 with phosphate buffer at pH 2. The solution is analyzed with UPLC instrument and the amount of methionine converted is calculated. If the protein is bound and active, N-acetyl methionine is converted into methionine. At the experimental conditions used, it was possible to discriminate between N-acetyl methionine and DL-methionine in the solution.

Method summary: Flow rate 0.5 ml/min. Injection volume: 2 µl Mobile phase A: 15 mM $KH_2PO_4$ at pH 2. Mobile phase B: Acetonitrile. Isocratic run: 90% A/10% B. Column temperature: 30° C. Analysis time per sample: 2 minutes.

Tools and Instruments

Millex® Syringe Filters, 33 mm diameter, PVDF Membrane, Pore Size 0.22 µm was purchased from Merck KGaA, Darmstadt, Germany.

Sterile Nunc Non-treated Multidishes, Product Code 150787, 48-well plate. Sterile Treated Multidishes, 96-well plate.

Sterile Black Multidishes with Transparent Bottom, 96-well plate.

Varioskan LUX, Thermo Scientific, Multimode Microplate Reader. Used to measure Absorbance and Fluorescence of samples in a 96-well plate format. Orbital incubator for inoculum preparation: SI500. manufacturer: Stuart (United Kingdom)

Thermo-Shaker for multiwell plates: PST-60HL-4. Manufacturer: bioSan (Latvia).

UPLC Instrument. Name: Acquity. Manufacturer: Waters (USA).

Column used within the UPLC instrument. Name: Primesep 100. Patricle size: 5 µm. ID: 2.1×50 mm. Manufacturer: Sielc Tech (USA).

Biofilm Quantification Assays

The alamarBlue™ Cell Viability Reagent solution was purchased from Invitrogen. The alamarBlue is an established and widely used cell metabolic activity indicator, available since 1993. In the present work, it was used to assess the amount of viable bacteria within the biofilm deposited over the tested material surface. The solution of alamarBlue is a cell viability assay reagent which contains the cell permeable, non-toxic and weakly fluorescent blue indicator dye called resazurin. Resazurin is converted into resorufin in response to cellular metabolic reduction. This oxidation reduction indicator is blue in its oxidized form and pink in the reduced one. Additionally, the reduced form is highly fluorescent and detected with Excitation Wavelength of 560 nm and Emission Wavelength of 590 nm.

The intensity of fluorescence produced is directly proportional to the number of living cells and reflects quantitatively cell viability and cytotoxicity parameters.

Bacterial cells attached to a surface (biofilm) were studied after the addition of alamarBlue solution in Phosphate Buffered Saline solution and incubated for 2-4 h at 37° C.

The hypothesis was that lower fluorescence at the values described above is a reflection of lower biofilm deposition on the tested material.

The Test Membrane Comprised:

1. Acylase-modified anionic nanocellulose membrane;
2. Non-quorum quenching molecule immobilized on nanocellulose membrane (Albumin or Gelatin from Bovine Skin).
3. Unmodified anionic nanocellulose membrane;
4. Pur-Zellin cellulose membrane (in some experiments where shown).

The membranes were inserted with sterile tweezers in a sterile NUNC 48-well plate and incubated with liquid culture of *Pseudomonas aeruginosa* PAO1 (prepared as described above) at 37° C. and at different shaking rpm values for 24 h.

The membranes were carefully transferred to a Black 96-well plate and rinsed with sterile phosphate buffered saline solution three times. The solution of Alamar Blue was prepared using a 10× stock, diluted to 1× with sterile PBS and using aluminum foil when necessary, in order to prevent the interaction of the solution with light. Alamar Blue 1× solution (200 µl) was added to each well and incubated at 37° C. and 250 rpm for 2-4 h. The membranes were removed from the wells, and the fluorescence was measured from the liquid solution.

Pyocyanin Determination Assay

*P. aeruginosa* is an opportunistic pathogen capable of producing a wide variety of virulence factors including lipopolysaccharides, proteases, exotoxins, pyocyanin, exopolysaccharides. Many of the extracellular virulence factors have been shown to be regulated by quorum-sensing signals.

As a result, the quantification of one of the virulence factors mentioned above is a useful method in order to study the quorum sensing process in *P. aeruginosa*.

Pyocyanin is a green, hydrophobic molecule produced by *P. aeruginosa* strain in vitro after the exponential growth phase is reached. It is extracted from the media using dichloromethane and therefore converted to a pink product with 0.2 N HCl in order to be detectable using Absorbance determination at 388 nm.

After incubation for 24 h of the test membranes, 150 µl of each culture triplicate were added to a test tube containing 450 µl of dichloromethane. A total amount of 450 µl for each sample type was added to a single test tube, to ensure enough pyocyanin to be detected using the method chosen.

At this stage, at the bottom there was dichloromethane and the media is on the top. Each Eppendorf was vigorously vortexed for 10 s and centrifuged at 6000 rpm for 5 minutes. Then 300 µl of dichloromethane solution in each test tube were transferred to another test tube containing 300 µl of HCl 0.2 N. To ensure correct pipetting, the tip had to be pre-conditioned with dichloromethane in order to prevent leakage of dichloromethane from the tip. The vortexing and centrifugation step was repeated again.

Then 100 µl of each HCl 0.2 N solution was transferred to a 96-well plate and the absorbance at 388 nm was monitored.

Results

The study of Lot 119171917t nanocellulose membrane (UPM).

The deposition of *P. aeruginosa* biofilm on 119671917t membranes was investigated using alamarBlue metabolic activity assay and pyocyanin quantification using the methods described in previous. The amount of lot 119671917t nanocellulose was 10 ml that was used entirely to test the activity of the modified material on *P. aeruginosa*.

The parameters investigated of were the effect of pH value of protein solution and the purification of acylase.

Figure 3:
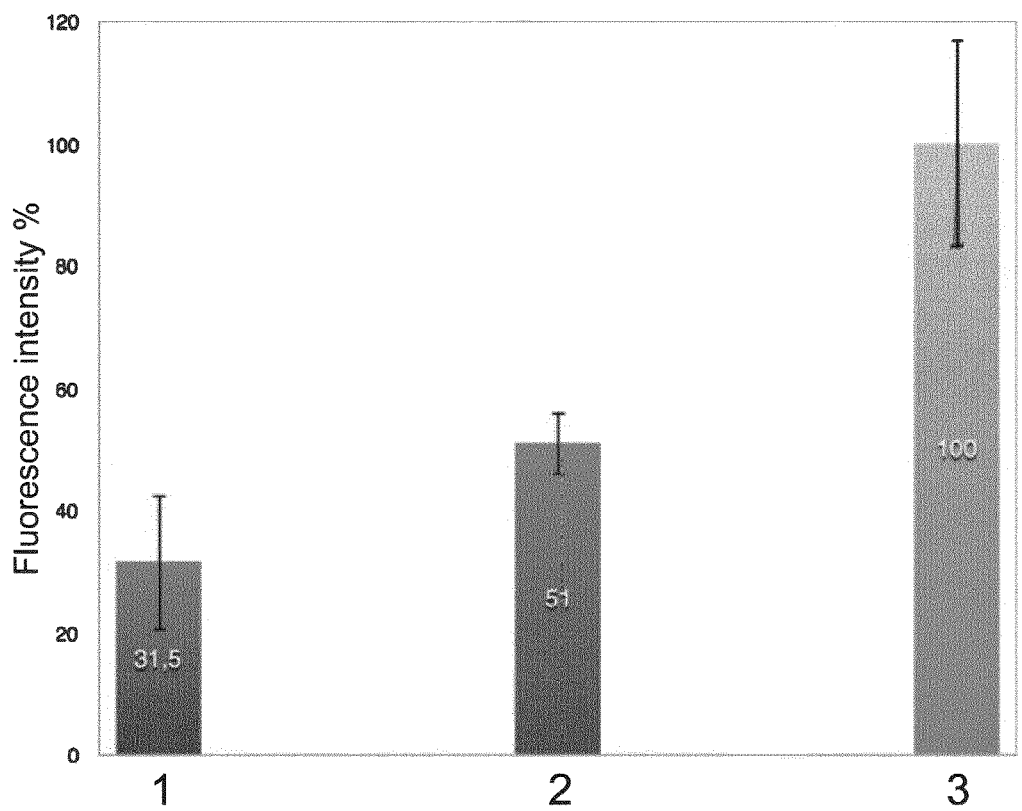
FIG. 3 shows alamarBlue analysis of P. aeruginosa biofilm on 119671917t nanocellulose membrane. 1=Condition A: 119671917t+protein immobilized at pH 7 (31.5%), 2=Condition B: 119671917t+protein immobilized at pH 6 (51%), 3=Control: 119671917t+albumin immobilized (100%)

As reported in FIG. 3, different pH values of acylase solution in MES buffer were tested against the metabolic activity of *P. aeruginosa* biofilm bound to the membranes.

The concentration of EDC solution in each well was 20 mM, while the concentration of sulfo-NHS was 30 mM. The activation time was 30 minutes at 700 RPM. After the activation of nanocellulose membranes, each well was rinsed with 600 µl of MES 20 mM buffer at pH 6 and this step was repeated two times. The solution of acylase was added to each rinsed well, 250 µl were added. The immobilization time was 3 hours with 500 RPM shaking. After the immobilization reaction, each well was rinsed with 800 µl of Glycine buffer 20 mM at pH 6.5. Albumin was used as a control, since it is not a quorum quenching protein, and immobilized using the same approach for Acylase.

Figure 4:
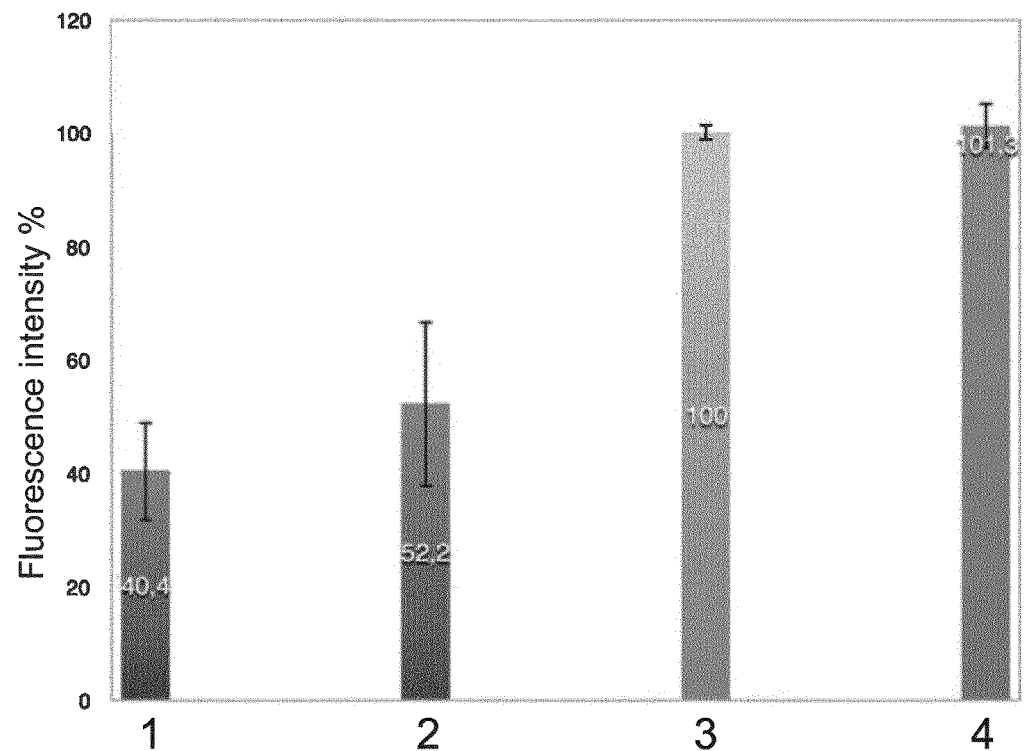
FIG. 4 shows alamarBlue analysis of P. aeruginosa biofilm on 119671917t nanocellulose. 1=Condition C: 119671917t+acylase purified (40.4%), 2=Condition D: 119671917t+acylase not purified (52.2%), 3=Control 1, 119671917t+albumin (100%), 4=Control 2: 119671917t (101.3%)

FIG. 4 shows the metabolic activity of *P. aeruginosa* biofilm. The parameter was the purification level of acylase. Purified acylase solution was obtained by dialysis using Snake Skin (Thermo Fisher) dialysis tube with cut-off of 10 kDa. 20 ml of the protein solution were inserted into a dialysis bag and positioned in a 2 l glass contained under stirring at 20° C. The buffer used was MES at pH 7. After the buffer solution was added, the removal of unwanted molecules from the protein solution was carried out for one week. The buffer was removed daily.

Figure 5:
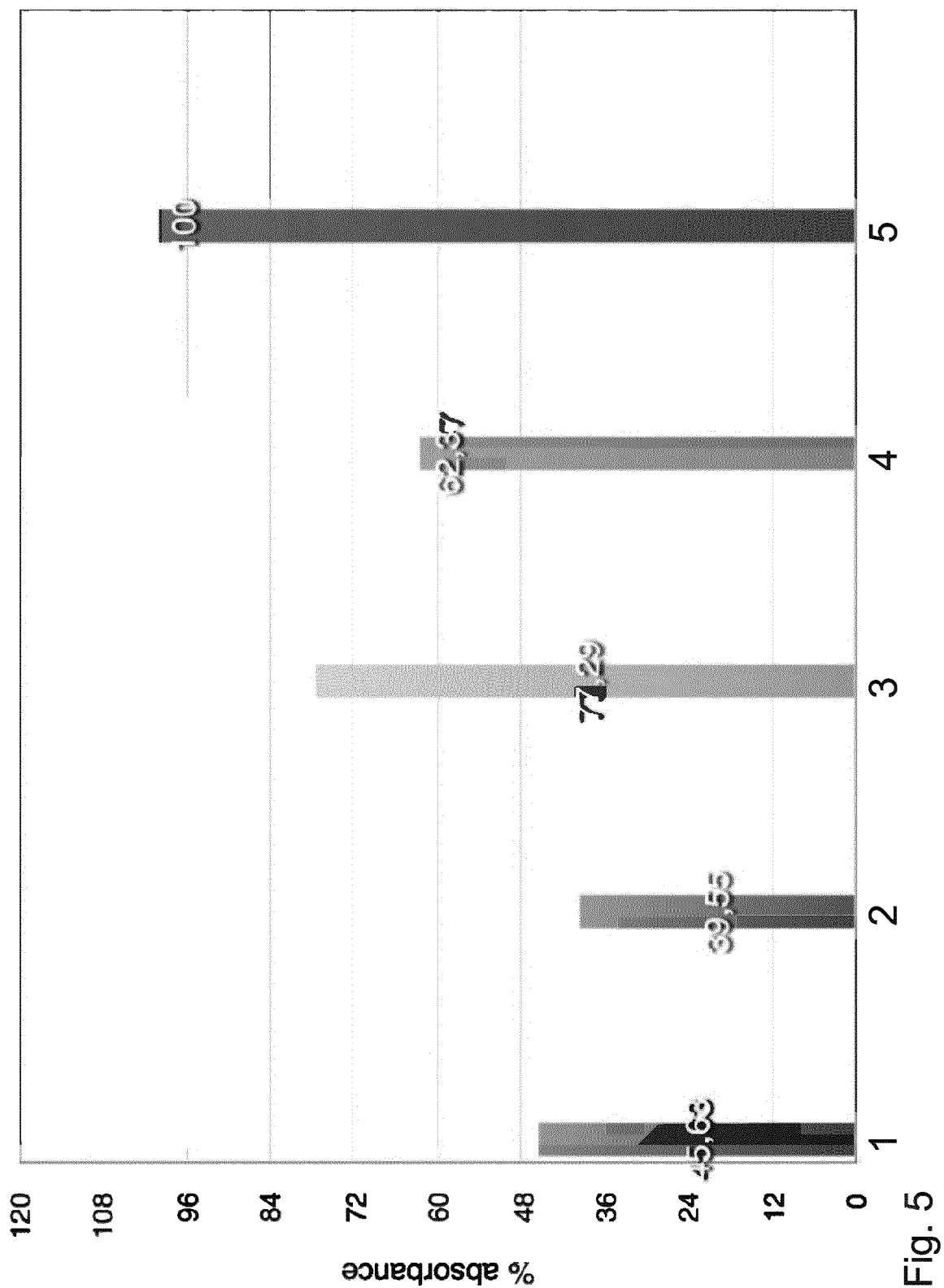
FIG. 5 shows P. aeruginosa pyocyanin quantification. 1=Condition C: 119671917t+acylase purified (45.63%), 2=Condition D: 119671917t+acylase not purified (39.55%), 3=Control 1, 119671917t+albumin (77.29%), 4=Control 2: 119671917t (62.37%), 5=Control 3: PAO1 culture only (100%)

The production of virulence factors and the effective quorum quenching activity of nanocellulose membranes was tested as reported in FIG. 5.

To each well containing *P. aeruginosa* culture and the tested membrane, 150 µl were taken and inserted into a test tube containing 450 µl of dichloromethane. The test was not carried out in triplicate, since the level of pyocyanin produced was too low and each triplicate (i.e. 150 µl×3) was reunited into one test tube. The remaining steps are available in the Materials and Methods chapter.

Data normalization was done according to the fact that the maximum amount of pyocyanin is produced by the *P. aeruginosa* culture with no membranes inside the well.

The Study of 11888 Nanocellulose Membrane (UPM).

The nanocellulose lot 11888 was used to study activity of immobilized acylase on 11888 nanocellulose membranes, *P. aeruginosa* biofilm metabolic activity and pyocyanin quantification. Unfortunately, no activity was measured with UPLC DL-methionine quantification and no promising results were obtained with AlamarBlue and pyocyanin quantification. The results are not shown and for this reason Lot 11885 was studied.

The Study of 11885 Nanocellulose Membrane (UPM).

Figure 12:
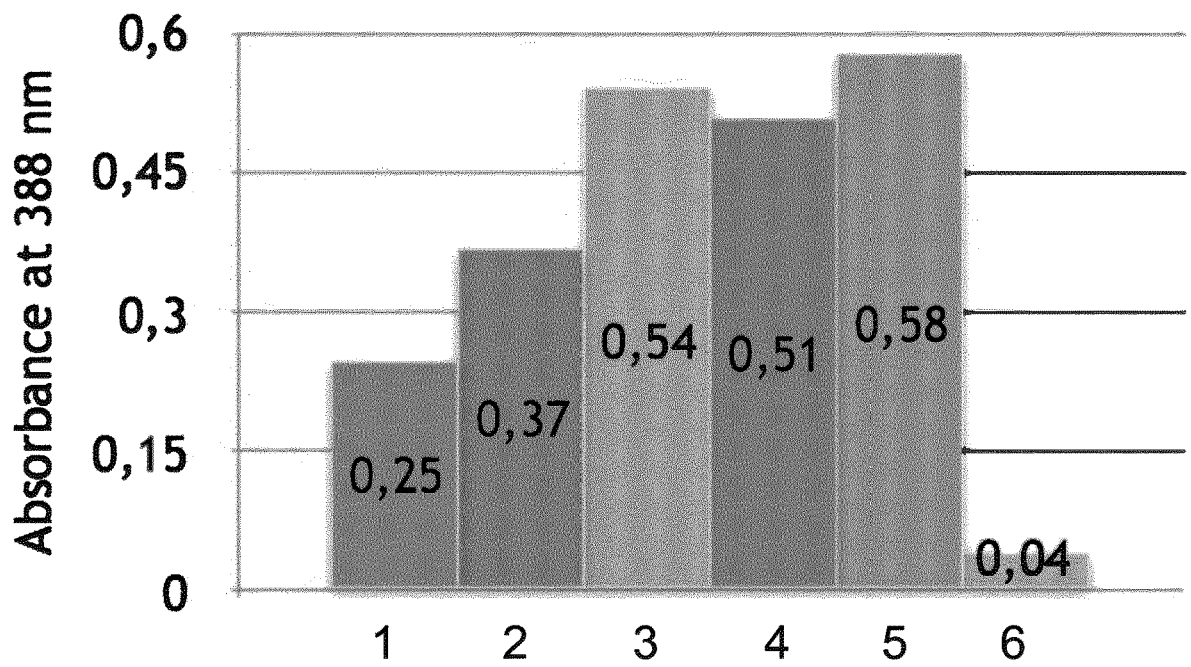
FIG. 12 shows pyocyanin quantification experiment 11885 membranes. 1=acylase, 2=gelatin, 3=nanocellulose only, 4=Pur-Zellin, 5=PAO1, 6=TSB

The nanocellulose lot 11885 was used to study activity of immobilized acylase on 11885 nanocellulose membranes, *P. aeruginosa* biofilm metabolic activity and pyocyanin quantification. The activity of immobilized acylase on 11885 was investigated with UPLC and several parameters were analyzed. Controls containing N-acetyl methionine, buffer solution, reagents without protein were used and data is not shown. The pyocyanin quantification results are shown in FIG. 12.

Figure 6A:
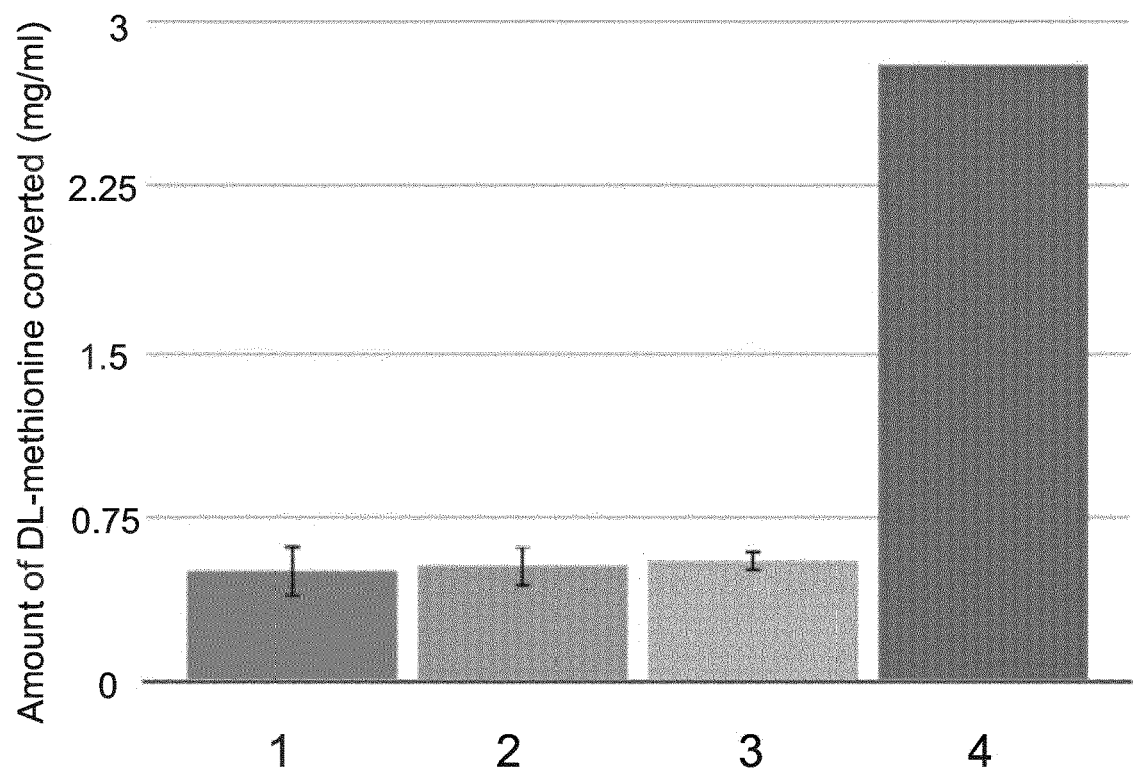
FIG. 6 shows the effect of differently sterilization methods on the immobilization and activity of acylase immobilized on 11885 nanocellulose membranes, against N-acetyl methionine at 37° C. with no shaking (FIG. 6A) and shaking at 250 RPM (FIG. 6B). 1=autoclaved 11885 (A: 0.51, B: 0.66), 2=ethanol sterilized 11885 (A: 0.52, B: 0.68), 3=not sterilized 11885 (A: 0.55, B: 0.58), 4=max theoretical amount (A: 2.80, B: 2.80)
Figure 6B:
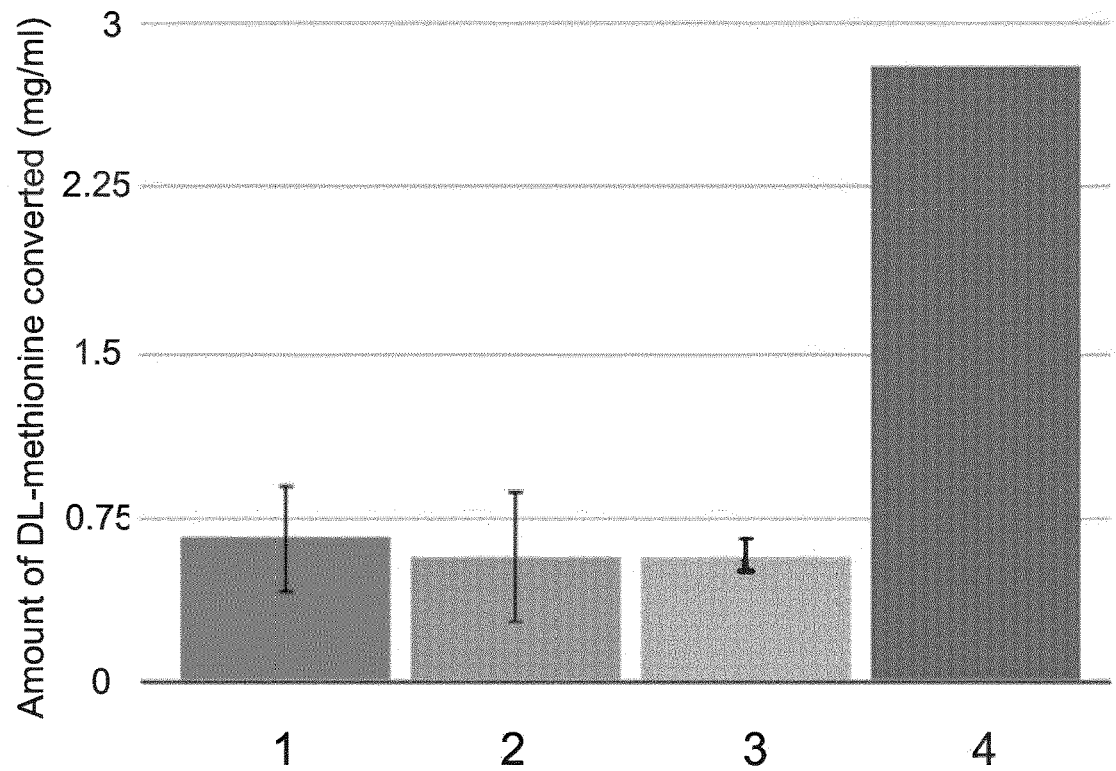
Figure 9A:
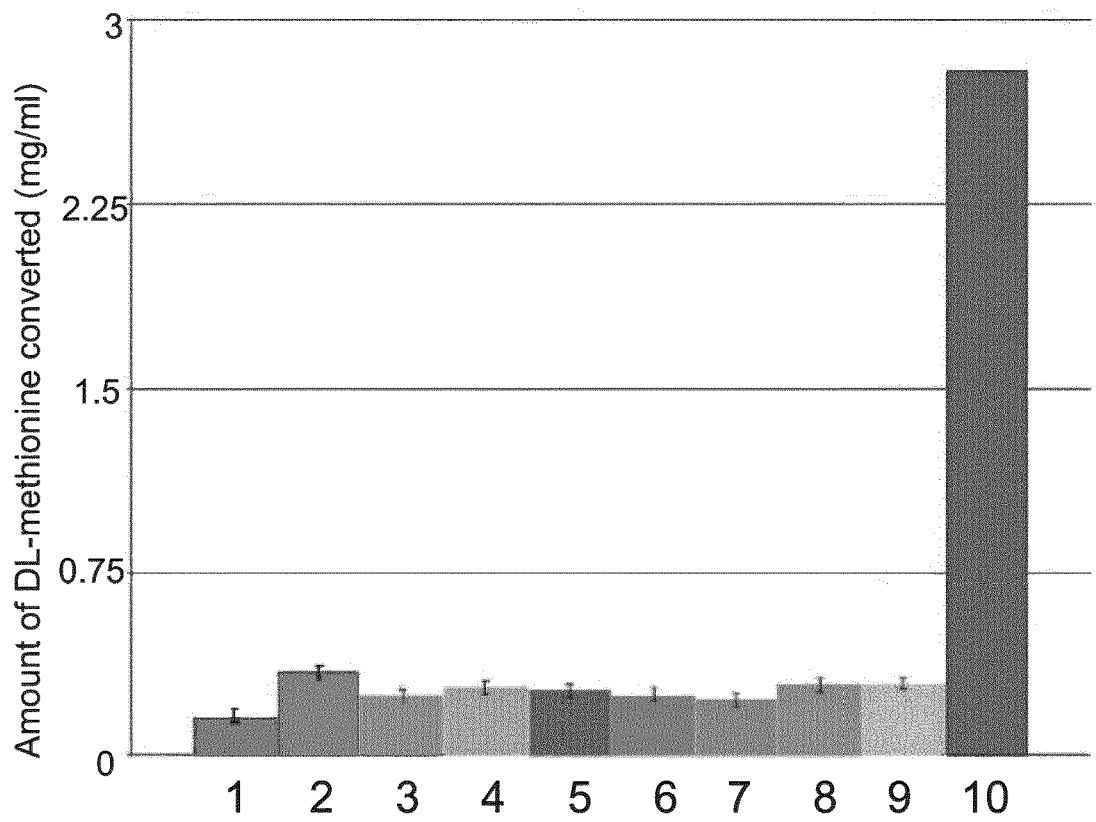
FIG. 9 shows two weeks activity of differently metal-activated acylase immobilized on 11885 nanocellulose membranes against N-acetyl methionine with 250 RPM shaking and 37° C. temperature. Two synthesis methods were tested, S1 (FIG. 9A) and S2 (FIG. 9B). 1=not activated acylase pH 6 (A: 0.163, B: 0.09), 2=not activated acylase pH 7 (A: 0.342, B: 0.35), 3=not activated acylase pH 7.5 (A: 0.244, B: 0.16), 4=$Co^{2+}$ activated acylase pH 6 (A: 0.277, B: 0.12), 5=$Co^{2+}$ activated acylase pH 7 (A: 0.266, B: 0.12), 6=$Co^{2+}$ activated acylase pH 7.5 (A: 0.247, B: 0.15), 7=$Mg^{2+}$ activated acylase pH 6 (A: 0.229, B: 0.12), 8=$Mg^{2+}$ activated acylase pH 7 (A: 0.289, B: 0.15), 9=$Mg^{2+}$ activated acylase pH 7.5 (A: 0.294, B: 0.10), 10=max theoretical amount (A: 2.80, B: 2.80)

The effect of the sterilization method (FIG. 6), the EDC and sulfo-NHS activation time (FIG. 7), the role of different acylase activating metals (FIG. 8), stability over the time at +4° C. (FIG. 9 and FIG. 10) and the effect of quenching solutions before and after protein immobilization (FIG. 11).

FIG. 4 shows the effect of different sterilization methods on the activity of immobilized acylase. Time point for the N-acetyl methionine conversion is 24 hours.

The concentration of EDC in each well was 65 mM and Sulfo-NHS was 18 mM. The immobilization reaction was carried out for 4 hours at 500 RPM. After the reaction, each well was quenched with HEPES buffer at pH 8. Time point for the N-Acetyl Methionine conversion is 24 hours.

Figure 7:
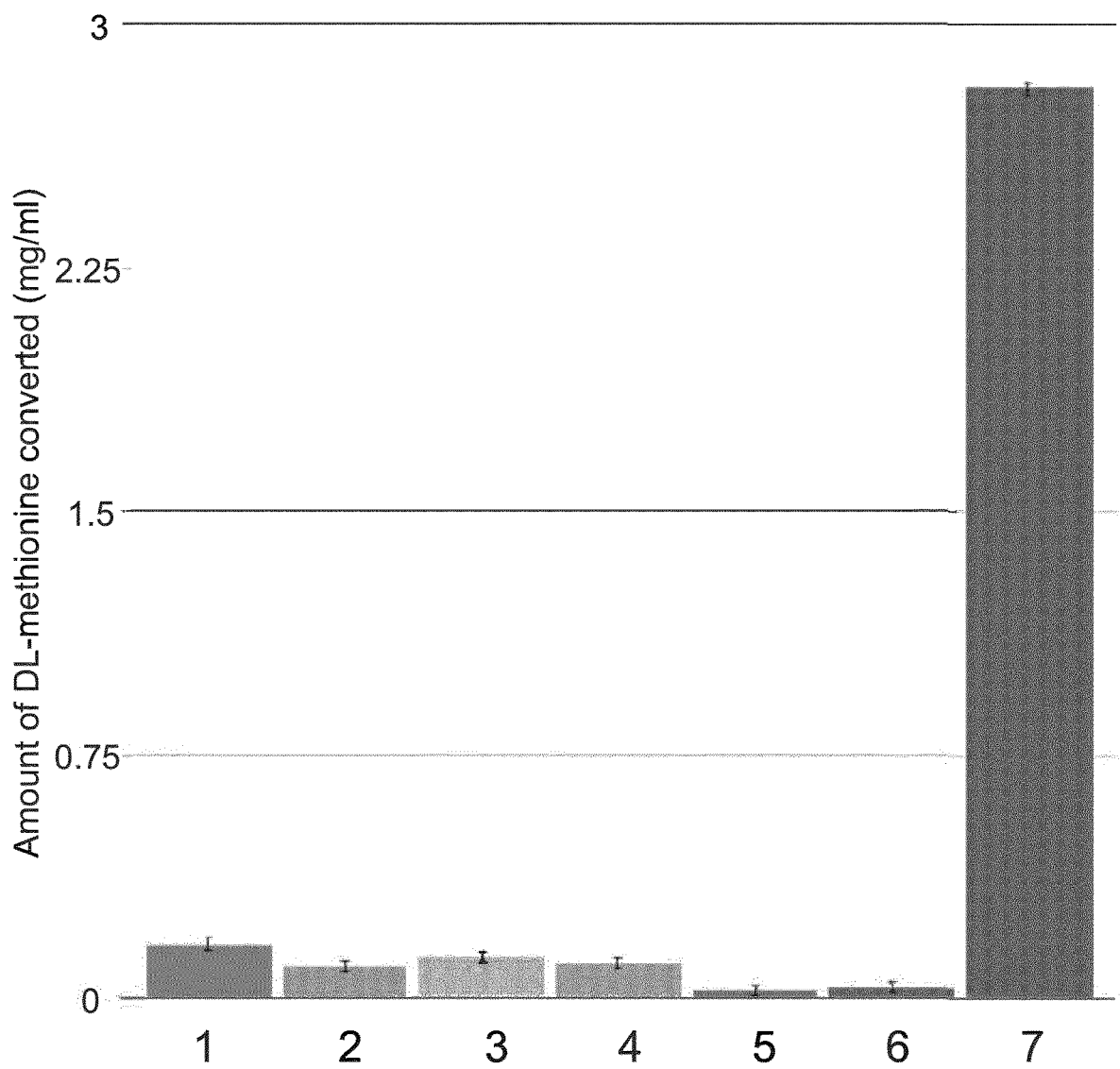
FIG. 7 shows the activity of differently activated 11885 nanocellulose membranes against N-acetyl methionine with 250 RPM shaking and 37° C. temperature. The purification of acylase and the activation time with EDC and Sulfo-NHS were tested. 1=15 min activation+purified acylase (0.164), 2=15 min activation+not purified acylase (0.094), 3=30 min activation+purified acylase (0.126), 4=30 min activation+not purified acylase (0.104), 5=reagents+purified acylase at the same time (0.021), 6=reagents+not acylase at the same time (0.03), 7=max theoretical amount (2.8)

FIG. 7 shows different effects of nanocellulose derivatization times. EDC and sulfo-NHS were respectively at the concentration 66 mM and 13 mM. The immobilization reaction was carried out in 4 hours. Acylase was dissolved in MES buffer pH 6 with 150 mM NaCl and MES pH 6 with 150 mM NaCl was used to dialyze the protein when necessary.

The reagents reacted with nanocellulose for 15 minutes, 30 minutes and also the immediate addition of protein solution, EDC and sulfo-NHS was tested. Time point for the N-Acetyl Methionine conversion is 4 hours.

The effect of metal ions on metalloenzymes is widely known, and the same is for acylase enzyme. The effect of cobalt chloride hexahydrate, magnesium chloride and no activating metal was tested as shown in FIG. 8.

The concentration of cobalt chloride hexahydrate was 0.5 mM and magnesium chloride was 1 mM. The concentration was chosen as indicated by the provider of the protein (Sigma-Aldrich).

Additionally, different pH values were tested and protein was not purified. Different pH values are believed to control the reactivity of N-terminal amine in the protein molecule, because of different protonation levels at different pH values. EDC and sulfo-NHS concentration were different from synthesis method 1 (51, FIG. 8A) and synthesis method 2 (S2, FIG. 8B). 51 refers to the utilization of EDC at the concentration of 40 mM and sulfo-NHS at 10 mM. The condition S2 had EDC at the concentration of 10 mM and Sulfo-NHS at 40 mM.

The pH value of each protein solution was checked after the addition of protein powder. Cobalt chloride was dissolved in MQ water at the concentration of 150 mM and then an aliquot was transferred to the protein solution vial. Magnesium chloride was dissolved in MQ water at the concentration of 200 mM and then an aliquot was transferred into protein solution vial.

The stability of immobilized protein was studied. Additionally, the effect of 51 and S2 parameters on protein stability was investigated.

Figure 9B:
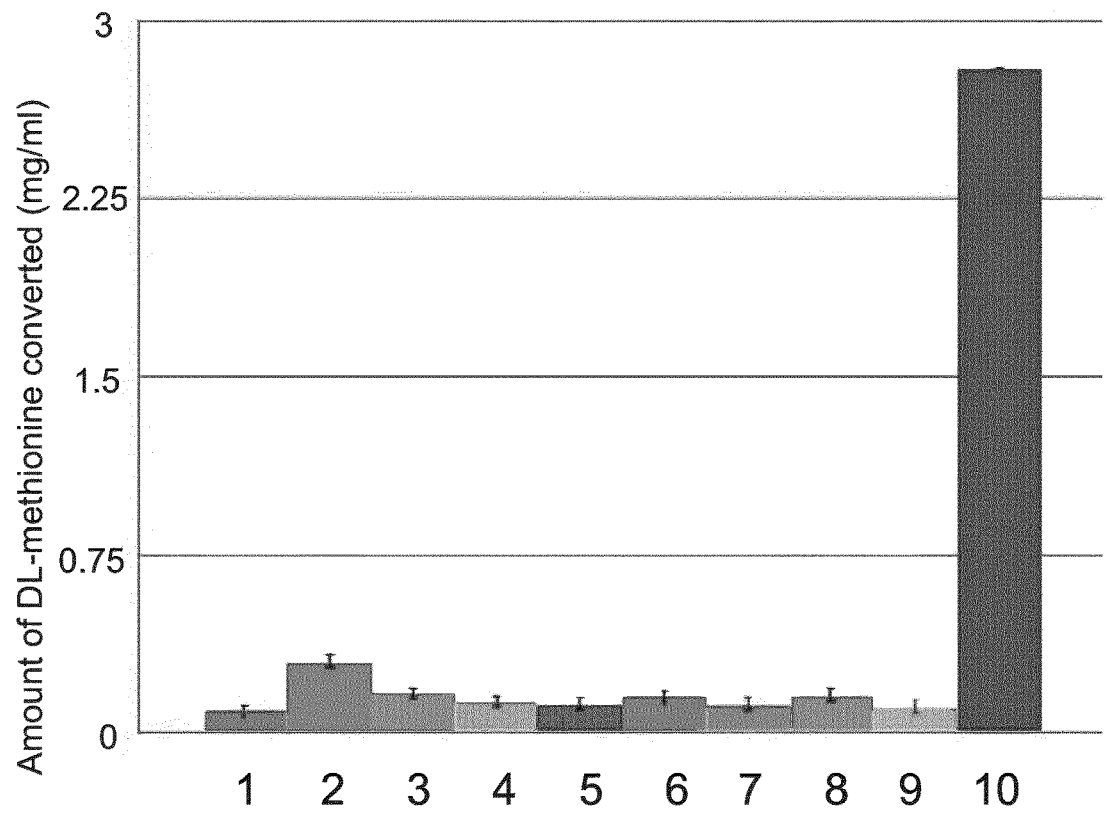
Figure 10A:
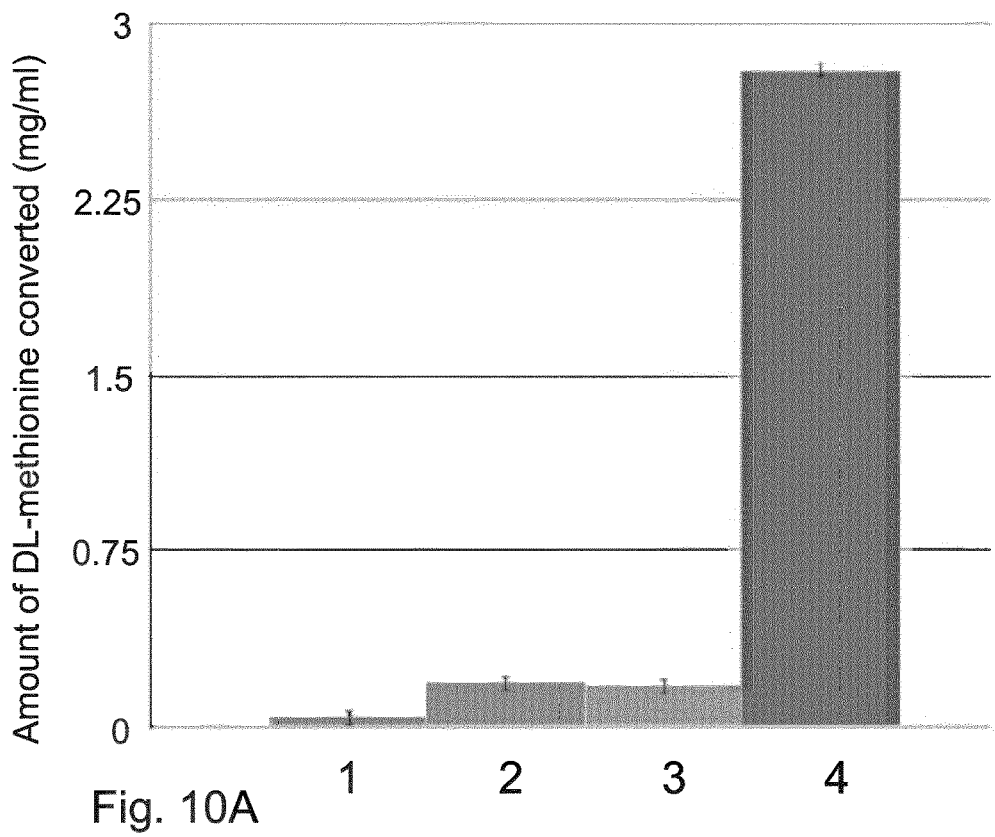
FIG. 10 shows one month activity of differently sterilization methods on the immobilization and activity acylase immobilized on 11885 nanocellulose membranes, against N-acetyl methionine at 37° C. with no shaking (FIG. 10A) and shaking at 250 RPM (FIG. 10B). 1=autoclaved 11885 (A: 0.036, B: 0.071), 2=ethanol sterilized 11885 (A: 0.184, B: 0.201), 3=not sterilized 11885 (A: 0.173, B: 0.218), 4=max theoretical amount (A: 2.80, B: 2.80)

FIG. 9 shows activity quantification after two weeks. Acylase was immobilized on 11885 membranes, further stored at +4° C. for two weeks in HEPES 20 mM pH 8, 150 mM NaCl. The membranes were rinsed three times with HEPES 20 mM pH 8, 150 mM NaCl prior the experiment.

Figure 10B:
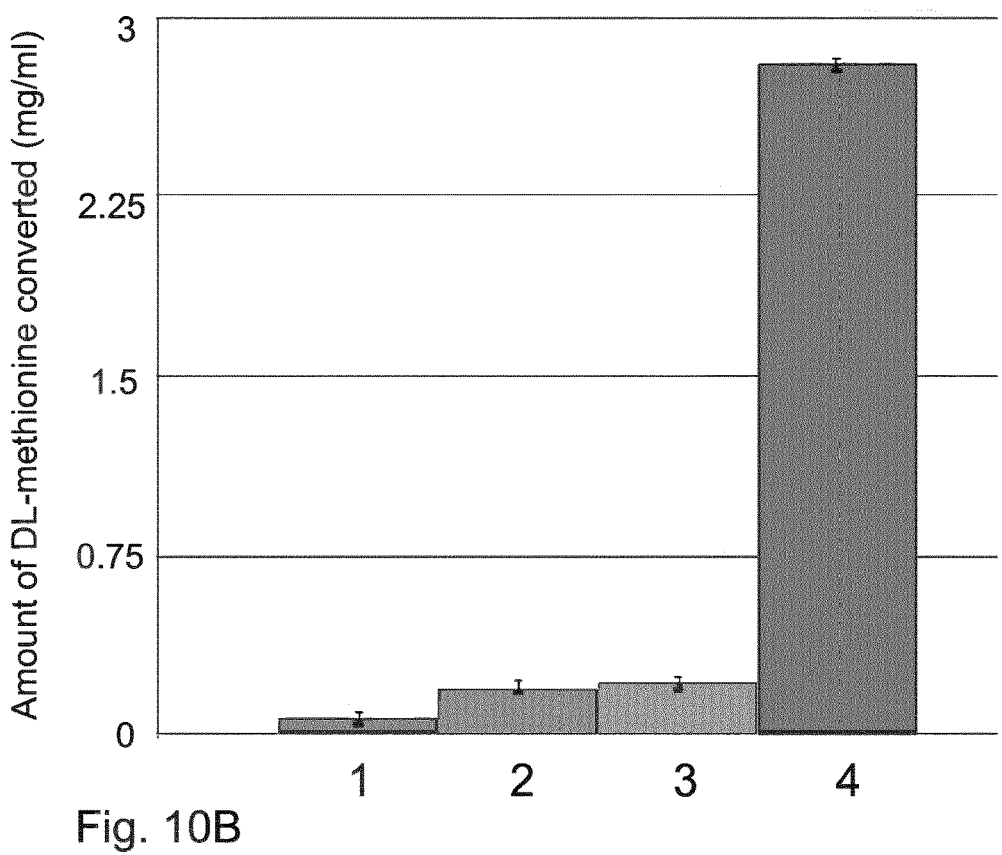
Figure 11:
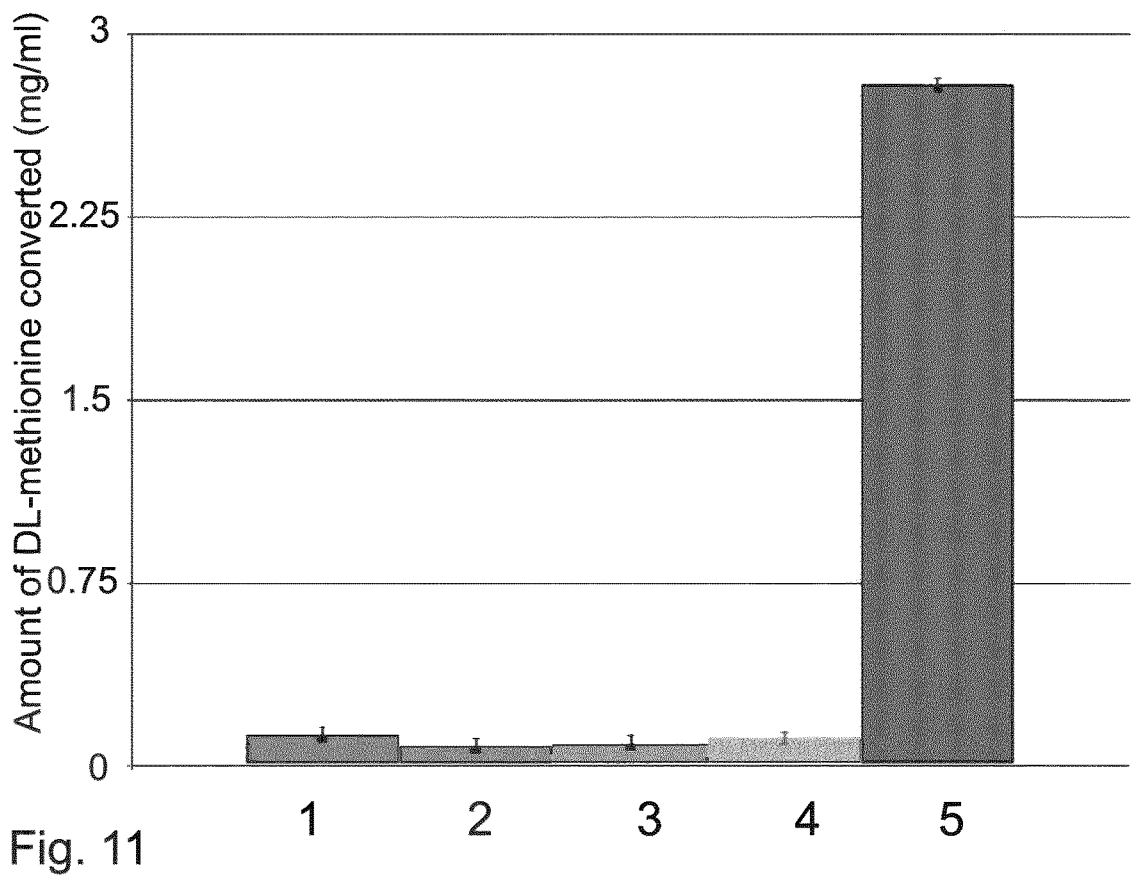
FIG. 11 shows the effect of different treatments on acylase activity, immobilized on 11885 nanocellulose membranes against N-acetyl methionine with 250 RPM shaking and 37° C. temperature. BME=2-mercaptoethanol. 1=without BME, quench pH 8 (0.127), 2=with BME, quench pH 8.6 (0.079), 3=without BME, quench pH 8.6 (0.092), 4=with BME, quench pH 8 (0.111), 5=max theoretical amount (2.80)

As reported in FIG. 10, the sterilized and not sterilized membranes with immobilized acylase were tested after one month in HEPES buffer at pH 8. The buffer used was MES 20 mM pH 6 with 150 mM NaCl for pH 6, HEPES 20 mM pH 7 with 150 mM NaCl for pH 7 and HEPES 20 mM pH 7.5 with 150 mM NaCl for pH 7.5.

Given that reactive species may interfere with acylase activity if not properly quenched. 2-mercaptoethanol (BME) was used to quench any reactive EDC within the well after the activation and derivatization of nanocellulose with EDC and sulfo-NHS (FIG. 11). Additionally, two different pH buffers were used to check the effect of slightly different pH values used when rinsing the membranes after the immobilization of Acylase.

Rising the pH above 8 is reported to hydrolyze NHS esters formed. BME was used at the concentration of 60 mM. Buffer pH 8 was HEPES buffer saline 20 mM, 150 mM NaCl. Buffer pH 8.6 was bicarbonate buffer 20 mM with 150 mM NaCl. The immobilization reaction with Acylase was performed in 2 hours. Quenching with BME was performed in 10 minutes. Quenching with buffers is performed overnight (approx. 14 hours).

Figure 13:
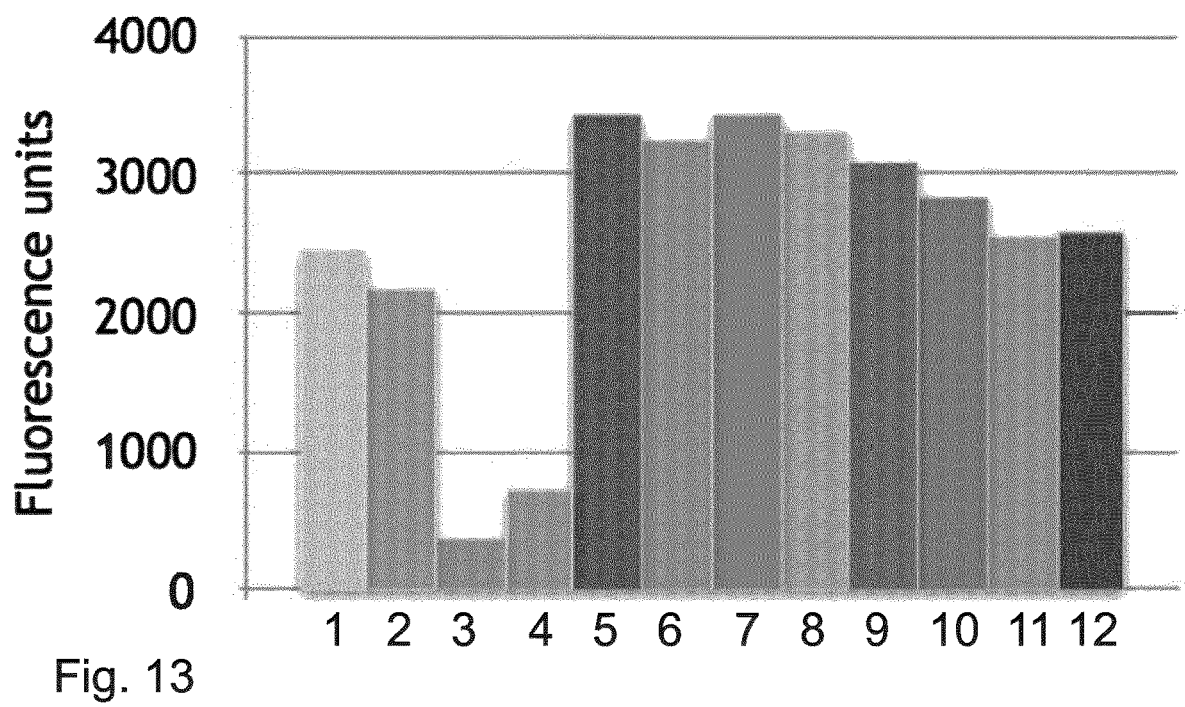
FIG. 13 shows alamarBlue determination of metabolic activity of P. aeruginosa biofilm on nanocellulose 11885 membrane and Pur-Zellin medical grade cellulose with different conditions. 1=acylase C1, 2=acylase C2, 3=acylase C3, 4=acylase C4, 5=gelatine C1, 6=gelatine C2, 7=gelatine C3, 8=gelatine C4, 9=nanocellulose only, 10=nanocellulose only, 11=Pur-Zellin, 12=Pur-Zellin

The determination of *P. aeruginosa* metabolic activity was performed using alamarBlue metabolic activity indicator, as shown in FIG. 13.

The Conditions Tested were Four:

C1: No deactivation of excess EDC with BME, final quenching overnight with HEPES pH 8

C2: Deactivation of excess EDC with BME 60 mM for 10 minutes, final quenching overnight with HEPES 20 mM, 150 mM NaCl at pH 8

C3: No deactivation of excess EDC with BME, final quenching overnight with Bicarbonate Buffer 20 mM, 150 mM NaCl at pH 8.6

C4; Deactivation of excess EDC with BME 60 mM for 10 minutes, final quenching overnight with Bicarbonate Buffer 20 mM, 150 mM NaCl at pH 8.6.

Figure 14:
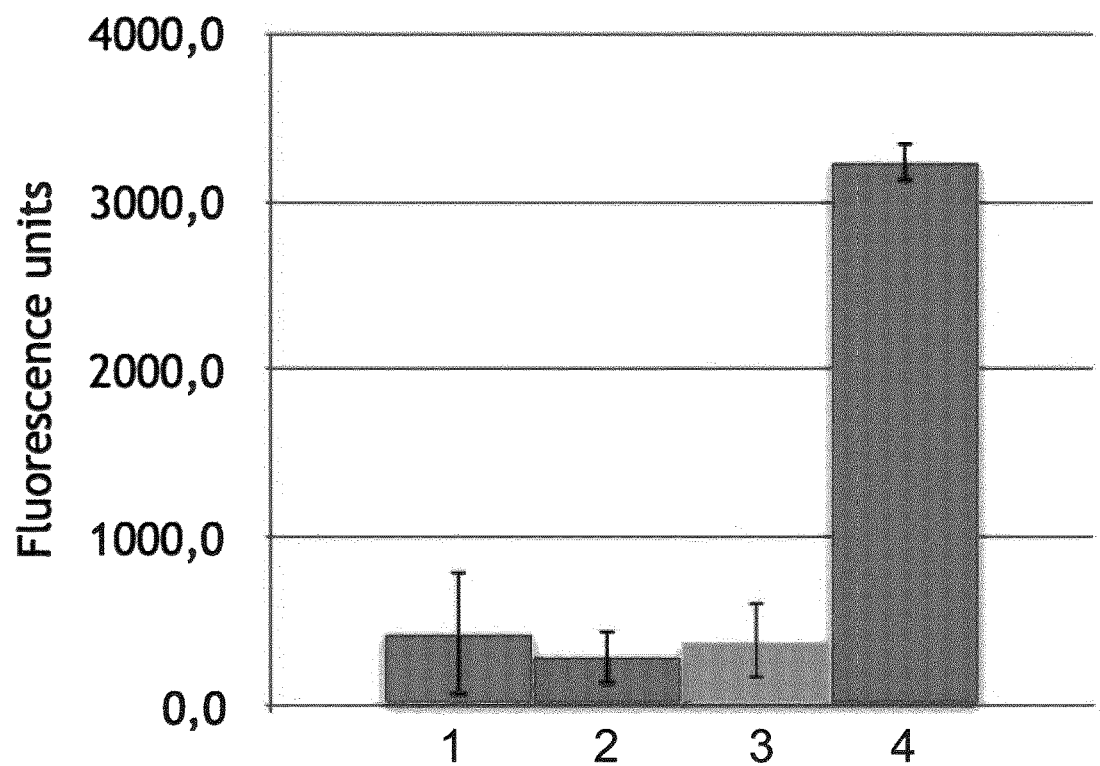
FIG. 14 shows alamarBlue determination of metabolic activity of P. aeruginosa biofilm on nanocellulose 11885 membrane and Pur-Zellin medical grade cellulose. 1=acylase, 2=gelatin, 3=nanocellulose only, 4=Pur-Zellin

EDC concentration was 40 mM and sulfo-NHS concentration was 10 mM. Gelatin was used instead of Albumin, to provide less unspecific interaction. Gelatin from bovine skin, Type B, was purchased from Sigma-Aldrich. Gelatin solution was obtained dissolving gelatin at the concentration of 1 mg/ml in MES 20 mM Buffer at pH 6. The determination of metabolic activity of *P. aeruginosa* biofilm was performed using different parameters and the results are as shown in FIG. 14.

Acylase was dissolved at the concentration of 10 mg/ml in MES 20 mM buffer at pH 6 and not purified. Cobalt chloride was added at the concentration of 0.5 mM. EDC and sulfo-NHS added were at the concentration of 40 mM and 10 mM respectively. The activation time with EDC and sulfo-NHS was 15 minutes and acylase immobilization time was 3 hours.

Discussion

Based on the data showed in the previous chapter, it was clear that different nanocellulose lots provide different immobilization yields and quorum quenching activities.

Lot 119671917t had a different impact on the development of bacterial biofilm than lot 11885.

The immobilization of acylase on Lot 119671917t provided 69% reduction of the biofilm when protein solution was at pH 7 (FIG. 3), 59.6% reduction when a purified protein solution was used (FIG. 4) and 47.8% when using a not purified protein solution (FIG. 4). In addition, pyocyanin levels were reduced up to 55% FIG. 5).

The results further obtained were based on lot 11885 and lot 11888 was discarded because no encouraging data was obtained.

In order to obtain a quorum quenching device based on 11885 nanocellulose and acylase, activity tests were performed to achieve better conditions for the immobilization of acylase and furthermore to maintain its activity after it was bound to the nanocellulose membrane surface.

The first successful data about activity of immobilized acylase on nanocellulose membranes was as indicated in FIG. 7. In a limited amount of time it was possible to monitor the presence of converted DL-methionine.

In addition, the sterilization process play a key role in the development of successful wound healing related materials. There was no difference between autoclavation, ethanol sterilization and no sterilization for the activity against N-acetyl methionine.

The quenching process of possible denaturing molecules that are generated from the reaction showed to be not effective to the increase of the activity of immobilized acylase (FIG. 11).

Figure 8A:
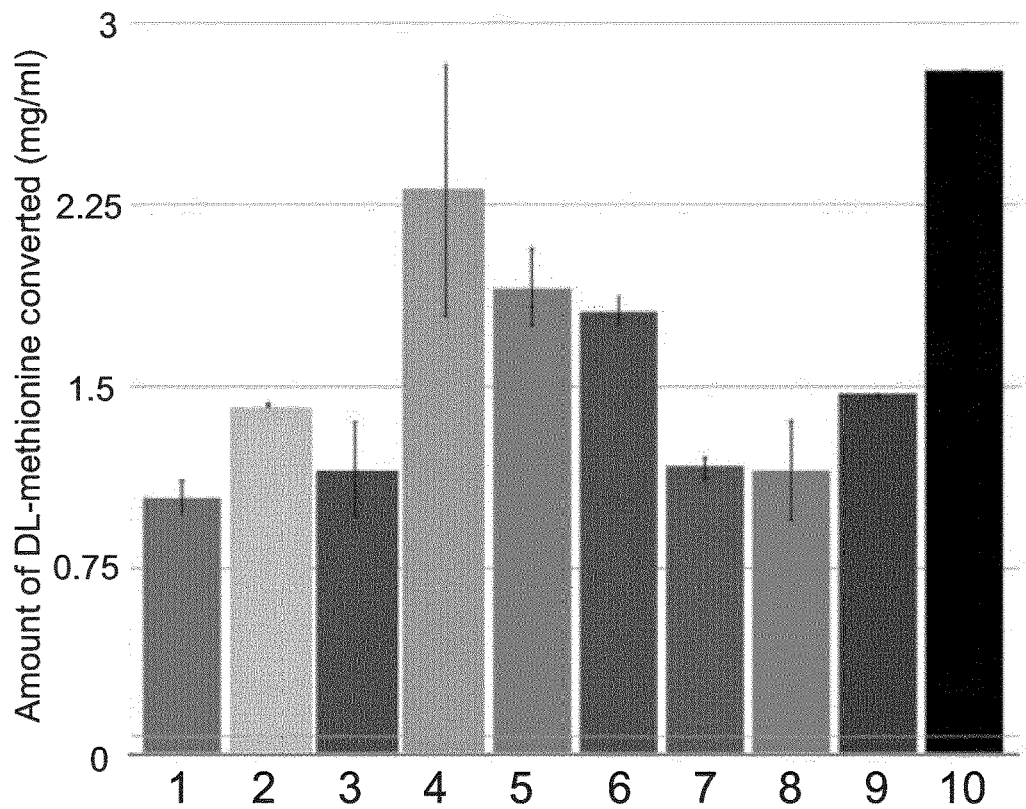
FIG. 8 shows the activity of differently metal-activated acylase immobilized on 11885 nanocellulose membranes against N-acetyl methionine with 250 RPM shaking and 37° C. temperature. Two synthesis methods were tested, S1 (FIG. 8A) and S2 (FIG. 8B). 1=not activated acylase pH 6 (A: 1.05, B: 0.87), 2=not activated acylase pH 7 (A: 1.43, B: 1.19)), 3=not activated acylase pH 7.5 (A: 1.16, B: 1.05), 4=$Co^{2+}$ activated acylase pH 6 (A: 2.31, B: 2.27), 5=$Co^{2+}$ activated acylase pH 7 (A: 1.91, B: 1.44), 6=$Co^{2+}$ activated acylase pH 7.5 (A: 1.92, B: 1.90), 7=$Mg^{2+}$ activated acylase pH 6 (A: 1.17, B: 1.41), 8=$Mg^{2+}$ activated acylase pH 7 (A: 1.15, B: 1.70), 9=$Mg^{2+}$ activated acylase pH 7.5 (A: 1.47, B: 1.69), 10=max theoretical amount (A: 2.80, B: 2.80)
Figure 8B:
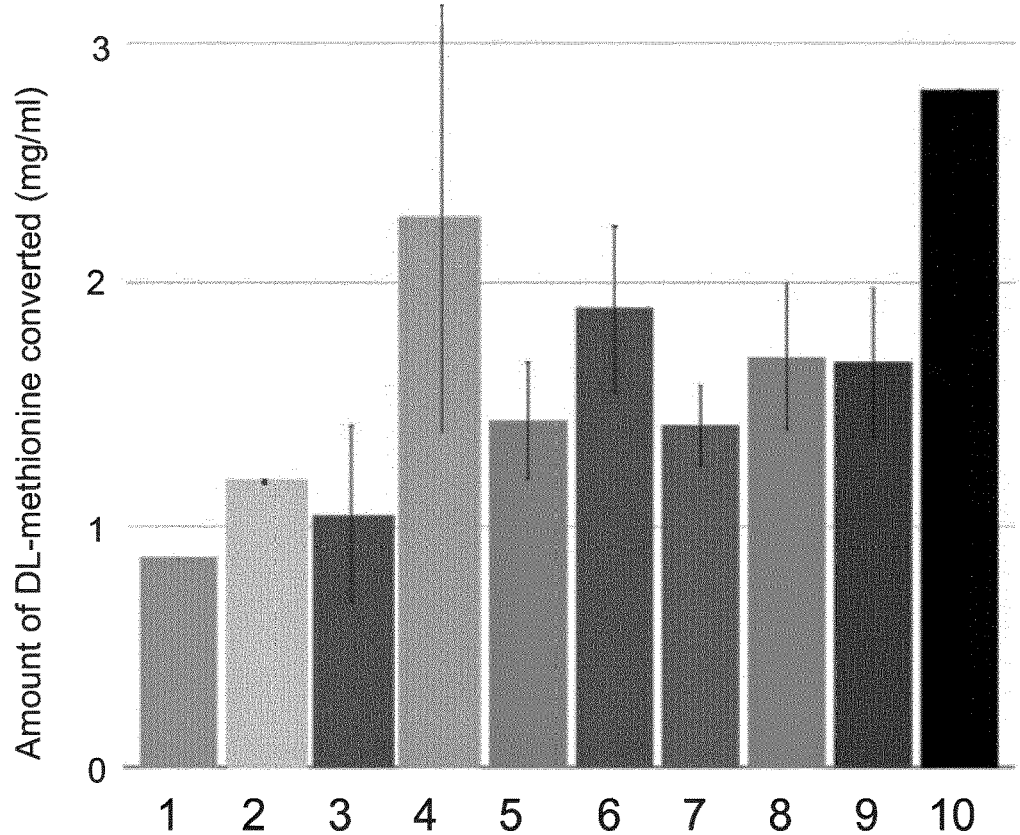

Metal activated membranes were stored at +4° C. for two weeks to monitor the effect of the storage and metal ions on the stability. Based on the median values from percentage, unactivated membranes maintained 20.4% of their activity after two weeks, while cobalt activated 13% and magnesium activated 22% of activity (FIGS. 8A and 9A). A free protein usually undergoes several chemical and physical degradation processes, while immobilized enzymes generally maintain their activity over the time without a complete loss of activity.

The sterilization process seems not to play a significant role for the activity of immobilized acylase when considering freshly prepared membranes and reactive sites seem to be maintained for the immobilization reaction.

When it comes to long term stability, this trend seems to change. The membranes were stored for one month at +4° C. in HEPES Buffer. The autoclaved membranes with acylase immobilized lost 93% of their activity (FIG. 10A). Ethanol sterilized membranes that were modified with acylase had reduced activity of 65% (FIG. 10A). A similar trend is maintained when considering not sterilized membranes modified with acylase, that reduce their activity by 69%. FIG. 10A).

Concerning the activity of acylase immobilized on 11885 nanocellulose against *P. aeruginosa*, the results were not equal to the ones obtained from lot 119671917. Pyocyanin quantification showed a lower decrease in virulence expression.

AlamarBlue metabolic activity test suggests that the quenching buffer at high pH (bicarbonate buffer at pH 8.6) has an effect on the activity of the immobilized acylase and the biofilm deposition is reduced by 87% with Condition 3 and by 75% when considering Condition 4 (FIG. 13). When an additional test was performed with the conditions mentioned in the previous chapter, it could not be possible to repeat that result.

CONCLUSIONS

Herein the ability of immobilized acylase to quench effectively quorum sensing in *P. aeruginosa* for wound healing purposes were studied. The complete development of materials and coatings that efficiently inhibit bacterial adhesion while reducing the high incidence of antibiotic resistance is a challenging topic.

Overall, different techniques were used in order to understand the immobilization reaction and obtain the best conditions that lead to the development of a solid protocol for further development of the project.

The properties of the quorum quenching nanocellulose material were investigated using three different nanocellulose lots. There was an encouraging activity when testing 1196719171t lot. The same results were not reached by lot11888 and partially by lot11885. The chemical difference between the lot tested could explain the different outcome.

From the activity assay with N-acetyl methionine with UPLC, it was possible to determine that the protein is immobilized on nanocellulose 11885 and it is stable. It was also possible to recover activity after one month.

Among all the possible proteins, acylase was chosen because of its very low cost and reported stability. The chemical modification based on EDC and sulfo-NHS is believed to be selective, efficient and not toxic for the material.

Because of many difficulties in the determination of the biofilm on a material, alamarBlue assay was identified as a rapid method to investigate metabolic activity of *P. aeruginosa* on the membrane. It was possible also to determine the amount of virulence factor pyocyanin that was excreted over the time.

The invention claimed is:

1. A method for preparing a medical product for covering tissue, such as skin, the method comprising
    providing nanofibrillar cellulose having an average diameter of 200 nm or less,
    providing a gauze,
    providing a bioactive molecule,
    incorporating the nanofibrillar cellulose to the gauze, and
    covalently bonding the bioactive molecule to the nanofibrillar cellulose,
    wherein the nanofibrillar cellulose is provided at a moisture content of, or adjusted to, 0-20% (w/w).

2. The method of claim 1, comprising preparing at least one layer comprising the nanofibrillar cellulose.

3. The method of claim 1, comprising carrying out the covalent bonding through primary amines or through sulfhydryl groups.

4. The method of claim 1, comprising carrying out the covalent bonding in an aqueous medium.

5. The method of claim 1, wherein the bioactive molecule is selected from proteins, peptides, nucleic acids, hormones, cytokines, photosensitizing molecules, and anti-cancer drugs.

6. The method of claim 1, wherein the bioactive molecule is a quorum quenching protein.

7. The method of claim 1, comprising providing the nanofibrillar cellulose at a moisture content of, or adjusting the moisture content of the nanofibrillar cellulose to the range of 1-10% (w/w).

8. The method of claim 1, wherein the nanofibrillar cellulose, when dispersed in water, provides a Brookfield viscosity of at least 2000 mPa·s, measured at a temperature of 20° C.±1° C., a consistency of 0.8% (w/w) and at 10 rpm.

9. The method of claim 1, wherein the nanofibrillar cellulose has an average diameter of a fibril in the range of 1-200 nm.

10. The method of claim 1, wherein the nanofibrillar cellulose is selected from anionically modified nanofibrillar cellulose, cationically modified nanofibrillar cellulose, unmodified nanofibrillar cellulose, and oxidized nanofibrillar cellulose.

11. The method of claim 1, comprising forming the medical product into a membrane, a patch, a plaster, a bandage, a dressing or a filter, or into a part of a plaster, a patch or a dressing.

12. A medical product for covering tissue comprising nanofibrillar cellulose having an average diameter of 200 nm or less, and a gauze, and
    a bioactive molecule covalently bound to the nanofibrillar cellulose,
    wherein the medical product has a moisture content in the range of 0-20% (w/w).

13. The medical product of claim 12, wherein the nanofibrillar cellulose is present as a layer.

14. The medical product of claim 13 having a moisture content in the range of 1-10% (w/w).

15. The medical product of claim 12, wherein the bioactive molecule is selected from proteins, peptides, nucleic acids, hormones, cytokines, photosensitizing molecules, and anti-cancer drugs.

16. The medical product of claim 12, wherein the bioactive molecule is a quorum quenching protein.

17. The medical product of claim 12, wherein the nanofibrillar cellulose, when dispersed in water, provides a Brookfield viscosity of at least 2000 mPa·s, measured at a temperature of 20° C.±1° C., a consistency of 0.8% (w/w) and at 10 rpm.

18. The medical product of claim 12, wherein the nanofibrillar cellulose has an average diameter of a fibril in the range of 1-200 nm.

19. The medical product of claim 12, wherein the gauze is a nonwoven gauze.

20. The medical product of claim 12 obtained with the method of claim 1.

21. The medical product of claim 12 in a form of a membrane, a patch, a plaster, a bandage, a dressing or a filter, or as a part of a plaster, a patch or a dressing.

22. A method for treating a subject, such as a human subject, the method comprising
    providing the medical product of claim 12, and
    applying the medical product onto a tissue of the subject.

23. The method of claim 22, wherein the bioactive molecule is a quorum quenching protein and the treatment is to suppress or prevent bacterial biofilm formation.

24. The method of claim 22 wherein the treatment is treatment of skin wounds or other skin damages or injuries and the method comprises applying the medical product onto the skin wound, damage, or injury.

25. The medical product of claim 12, wherein the nanofibrillar cellulose is selected from anionically modified nanofibrillar cellulose, cationically modified nanofibrillar cellulose, unmodified nanofibrillar cellulose, and oxidized nanofibrillar cellulose.

26. The medical product of claim 12, wherein the nanofibrillar cellulose is TEMPO oxidized nanofibrillar cellulose.

* * * * *